(12) United States Patent
McLane et al.

(10) Patent No.: US 9,365,608 B2
(45) Date of Patent: Jun. 14, 2016

(54) METHOD FOR TREATING DIABETES

(75) Inventors: Michael McLane, Southampton, PA (US); Inez Ruiz-White, Southampton, PA (US); Henry Wolfe, Glenmoore, PA (US)

(73) Assignee: Ohr Pharmaceutical, Inc., New York, NY (US)

( * ) Notice: Subject to any disclaimer, the term of this patent is extended or adjusted under 35 U.S.C. 154(b) by 645 days.

(21) Appl. No.: 12/676,701

(22) PCT Filed: Sep. 8, 2008

(86) PCT No.: PCT/US2008/010455
§ 371 (c)(1),
(2), (4) Date: Sep. 7, 2010

(87) PCT Pub. No.: WO2009/032321
PCT Pub. Date: Mar. 12, 2009

(65) Prior Publication Data
US 2010/0324004 A1    Dec. 23, 2010

Related U.S. Application Data

(60) Provisional application No. 60/970,467, filed on Sep. 6, 2007.

(51) Int. Cl.
*C07J 41/00* (2006.01)
*C07J 43/00* (2006.01)
*C07J 5/00* (2006.01)
*C07J 31/00* (2006.01)

(52) U.S. Cl.
CPC *C07J 5/00* (2013.01); *C07J 31/006* (2013.01); *C07J 41/0005* (2013.01); *C07J 41/005* (2013.01); *C07J 41/0011* (2013.01); *C07J 41/0055* (2013.01); *C07J 43/003* (2013.01)

(58) Field of Classification Search
USPC ............... 514/175, 176, 182, 169; 552/521; 540/106
See application file for complete search history.

(56) References Cited

U.S. PATENT DOCUMENTS

| | | | | |
|---|---|---|---|---|
| 5,192,756 A | * | 3/1993 | Zasloff et al. | 514/182 |
| 5,721,226 A | * | 2/1998 | Frye et al. | 514/169 |
| 5,733,899 A | * | 3/1998 | Frye et al. | 514/169 |
| 5,792,635 A | * | 8/1998 | Zasloff | 435/184 |
| 5,856,535 A | * | 1/1999 | Zasloff et al. | 552/521 |
| 6,262,283 B1 | * | 7/2001 | Kinney et al. | 552/521 |
| 6,388,108 B1 | | 5/2002 | Rao et al. | 552/521 |
| 6,962,909 B2 | * | 11/2005 | Zasloff et al. | 514/171 |
| 7,410,959 B1 | * | 8/2008 | Zasloff et al. | 514/182 |
| 2003/0171576 A1 | | 9/2003 | Kinney et al. | 540/34 |

FOREIGN PATENT DOCUMENTS

| | | | |
|---|---|---|---|
| WO | WO 94/20520 | 9/1994 | ............... C07J 41/00 |
| WO | 96/40151 A1 | 12/1996 | |
| WO | WO 96/40728 | 12/1996 | ............... C07J 41/00 |
| WO | WO 98/24800 | 6/1998 | ................ C07J 9/00 |
| WO | 02/06299 A2 | 1/2002 | |
| WO | WO 2007/064691 | 6/2007 | ........... A61K 30/575 |
| WO | 2007/124086 A1 | 11/2007 | |

OTHER PUBLICATIONS

Moore et al (Proc. Nati. Acad. Sci. USA, vol. 90, pp. 1354-1358, Feb. 1993, Biochemistry).*
Zasloff et al. (AN 2008:975200, HCAPLUS< abstract U.S. Pat. No. 7,410,959, US 20080221075).*
Zasloff et al. (AN 2002:72114, HCAPLUS, abstract WO 2002006299, U.S. Pat. No. 7,410,959).*
Zhang et al. (J.Org. Chem. 1998,63, 8599-8603).*
Zhang et al. (AN 1998:686662, HCAPLUS, DN 130:66662), abstract of J.Org. Chem. 1998,63, 8599-8603).*
International Search Report issued in PCT application No. PCT/US2088/010455.
Communication under Rule 71(3) EPC, Intention to Grant dated Sep. 3, 2015 issued in corresponding European Patent Application No. 08829680.1.
Okumura et al., "Formal Synthesis of Squalamine from Desmosterol", Chemical Pharmaceutical Bulletin, Pharmaceutical Society of Japan, 51(10)1177-1182 (Oct. 1, 2003).
Office Action dated May 26, 2014 issued by the Canadian Patent Office in corresponding Canadian Patent Application No. 2,697,744.
Office Action dated Jan. 22, 2015 issued by the Canadian Patent Office in corresponding Canadian Patent Application No. 2,697,744.
Office Action dated Jul. 9, 2013 issued by the European Patent Office in corresponding European Patent Application No. 08 829 680.1.
Office Action dated Feb. 12, 2015 issued by the European Patent Office in corresponding European Patent Application No. 08 829 680.1.
Extended European Search Report dated Nov. 13, 2012 issued by the European Patent Office in corresponding European Patent Application No. 08 829 680.1.

* cited by examiner

*Primary Examiner* — Sabiha N Qazi
(74) *Attorney, Agent, or Firm* — Morgan, Lewis & Bockius LLP

(57) ABSTRACT

This application is directed to the use of steroid compounds for the selective inhibition of the enzyme PTP1B in a mammal for the treatment of diabetes.

8 Claims, 4 Drawing Sheets

METHOD FOR TREATING DIABETES

RELATED APPLICATIONS

The present application is a U.S. National Phase Application of International Application No. PCT/US2008/010455, filed Sep. 8, 2008, which claims the benefit of U.S. Provisional Patent Application No. 60/970,467, filed Sep. 6, 2007, all of which are hereby incorporated by reference in their entirety.

FIELD OF THE INVENTION

This application is directed to the use of steroid compounds for the selective inhibition of the enzyme PTP1B in a mammal for the treatment of diabetes.

BACKGROUND OF THE INVENTION

Several aminosterol compounds have been isolated from the liver of the dogfish shark, *Squalus acanthias*. One of these compounds has been designated as 1436, the structure of which is shown in FIG. 1. Compound 1436 has been previously described in, e.g., U.S. Pat. Nos. 5,763,430; 5,795,885; 5,847,172; 5,840,936 and 6,143,738, each of which is incorporated by reference in its entirety, and has been shown to inhibit weight gain and suppress appetite, which leads to weight loss in animal models.

Diabetes is a major medical problem in the United States and increasingly so in the rest of the developed world. Type II diabetes in particular is caused primarily by the effects of a sedentary life style and a fat-rich diet. The diabetic individual is susceptible to medical problems directly related to his disease such as elevated serum cholesterol, high blood pressure, congenital obesity syndromes (including congenital leptin, pro-opiomelanocortin (POMC) and melanocortin-4 receptor (MC4R) deficiencies), and sleep apnea, especially in pickwickian syndrome. In addition, the accumulation of fat in the liver can progress to nonalcoholic steatohepatitis and cirrhosis. Another problem for obese diabetic individuals is an increased risk in any surgery that must cut through thick layers of fatty tissue that are highly vascularized and therefore prone to hemorrhage. Necessary surgery is frequently postponed until this diabetic patient can lose sufficient weight to make the risk of the operation acceptable.

Insulin is an important regulator of different metabolic processes and plays a key role in the control of blood glucose. Defects related to insulin synthesis and signaling lead to diabetes mellitus. Binding of insulin to the insulin receptor (IR) causes rapid autophosphorylation of several tyrosine residues in the intracellular part of the beta-subunit. Three closely positioned tyrosine residues (the tyrosine-1150 domain) must be phosphorylated to obtain maximum activity of the insulin receptor tyrosine kinase (IRTK), which transmits further signals via tyrosine phosphorylation of other cellular substrates, including insulin receptor substrate-1 (IRS-1) and insulin receptor substrate-2 (IRS-2).

Protein phosphorylation is a well-recognized cellular mechanism for transducing and regulating signals during different stages of cellular function (see, e.g., Hunter, Phil. Trans. R. Soc. Lund. B. 353: 583-605 (1998); Chan et al., Annu. Rev. Immunol. 12: 555-592 (1994); Zhang, Curr. Top. Cell. Reg. 35: 21-68 (1997); Matozaki and Kasuga, *Cell. Signal.* 8: 113-119 (1996)). There are at least two major recognized classes of phosphatases: (1) those that dephosphorylate proteins that contain a phosphate group(s) on a serine or threonine moiety (termed Ser/Thr phosphatases or dual specificity phosphatases or DSPs) and (2) those that remove a phosphate group(s) from the amino acid tyrosine (termed protein tyrosine phosphatases or PTPases or PTPs).

Several studies clearly indicate that the activity of the auto-phosphorylated IRTK can be reversed by dephosphorylation in vitro (reviewed in Goldstein, Receptor 3: 1-15 (1993)) with the tri-phosphorylated tyrosine-1150 domain being the most sensitive target for PTPases. This tri-phosphorylated tyrosine-1150 domain appears to function as a control switch of IRTK activity and the IRTK appears to be tightly regulated by PTP-mediated dephosphorylation in vivo (Faure et al., J. Biol. Chem. 267: 11215-11221 (1992)).

PTP1B has been identified as at least one of the major phosphatases involved in IRTK regulation through studies conducted both in vitro (Seely et al., Diabetes 45: 1379-1385 (1996)) and in vivo using PTP1B neutralizing antibodies (Ahmad et al., J. Biol. Chem. 270: 20503-20508 (1995)). Three independent studies have indicated that PTP1B knock-out mice have increased glucose tolerance, increased insulin sensitivity and decreased weight gain when on a high fat diet (Elchebly et al., Science 283: 1544-1548 (1999), Klaman et al., Mol. Cell. Biol. 20: 5479-5489 (2000), and Bence et al., Nature Med (2006)). Overexpression or altered activity of tyrosine phosphatase PTP1B can contribute to the progression of various disorders, including insulin resistance and diabetes (Ann. Rev. Biochem. 54: 897-930 (1985)). Furthermore, there is evidence which suggests that inhibition of protein tyrosine phosphatase PTP1B is therapeutically beneficial for the treatment of disorders such as type I and II diabetes, obesity, autoimmune disorders, acute and chronic inflammation, osteoporosis and various forms of cancer (Zhang Z Y et al., Expert Opin. Investig. Drugs 2: 223-33 (2003); Taylor S D et al., Expert Opin. Investig. Drugs 3:199-214 (2004); J. Natl. Cancer Inst. 86: 372-378 (1994); Mol. Cell. Biol. 14: 6674-6682 (1994); The EMBO J. 12: 1937-1946 (1993); J. Biol. Chem. 269: 30659-30667 (1994); and Biochemical Pharmacology 54: 703-711 (1997)). Agents that inhibit phosphatase activity and thereby inhibit dephosphorylation of the insulin signaling pathway, increase whole-body insulin sensitivity. This is therapeutically beneficial in treatment of insulin resistance associated with Type II diabetes and obesity.

In addition, it has been shown (Bence K K et al., Nat Med 8:917-24 (2006)) that neuronal PTP1B in the brain regulates body weight, adiposity and leptin action. Therefore, if a PTP1B inhibitor can cross the blood brain barrier it will not only sensitize the effect of insulin but also result in weight loss an added benefit in the treatment of type II diabetes and in addition the treatment of obesity and its complications.

There is also reported insulin resistance in Type I diabetes for which agents with PTP1B inhibitory activity would be a useful therapeutic. An insulin sensitizing agent in early type I diabetes or in a pre-diabetic statue might delay the onset of diabetes by increasing the sensitivity to insulin and thereby reducing the requirement for over-secretion of insulin from remaining insulin-producing beta-cells in the pancreas, i.e. sparing these cells from subsequent "burn-out" and death. It has also been shown (Jiang Z X and Zhang Z Y, Cancer Metastasis Rev. 2:263-72 (2008)) that inhibitors of PTP1B can prevent the growth of tumors and therefore be useful for the treatment of cancer.

The PTPase family of enzymes can be classified into two subgroups: (1) intracellular or nontransmembrane PTPases and (2) receptor-type or transmembrane PTPases. Most known intracellular type PTPases contain a single conserved catalytic phosphatase domain consisting of 220-240 amino acid residues. The regions outside the PTPase domains are believed to play important roles in localizing the intracellular PTPases subcellularly (Mauro, L. J. and Dixon J. E., TIBS 19: 151-155 (1994)). The first of the intracellular PTPases to be purified and characterized was PTP1B (Tonks et al., J. Biol. Chem. 263: 6722-6730 (1988)). Other examples of intracellular PTPases include (1) T-cell PTPase (TCPTP) (Cool et al., Proc. Natl. Acad. Sci. USA 86: 5257-5261 (1989)), (2) neuronal phosphatases STEP (Lombroso et al., Proc. Natl. Acad. Sci. USA 88: 7242-7246 (1991)), (3) PTP1C/SH-PTP1/SHP-1 (Plutzky et al., Proc. Natl. Acad. Sci. USA 89: 1123-1127 (1992)), (4) PTP1D/Syp/SH-PPT2/SHP-2 (Vogel et al., Science 259: 1611-1614 (1993); Feng et al., Science 259: 1607-1611 (1993)).

Receptor-type PTPases consist of (a) a putative ligand-binding extracellular domain, (b) a transmembrane segment, and (c) an intracellular catalytic region. The structure and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PIPases have two tandemly duplicated catalytic PTPase domains. The first PTPase receptor subtypes identified were (1) CD45 (Ralph, S. J., EMBO J. 6: 1251-1257 (1987)) and (2) LAR (Streuli et al., J. Exp. Med. 168:1523-1530 (1988)). Since then, many more receptor subtypes have been isolated and characterized, including, e.g., PTPalpha, PTPbeta, PTPdelta, PTPepsilon and PTPxi. (Krueger et al. EMBO J. 9: 3241-3252 (1990)).

Although agents have been identified for use as PTP1B inhibitors, such as the heteroaryl- and aryl-amino acetic acids described in WO 01/19831, WO 01/19830, and WO 01/17516, these agents do not exhibit separation of the inhibitory activity between PTP1B and TCPTP. Furthermore, because of the potential immunosuppressive effects resulting from inhibiting TCPTP, selective inhibition of PTP1B over TCPTP would make such agents more suitable for drug development as they could diminish or eliminate undesired side effects resulting from such nonselectivity.

Therefore, there is a need for a drug that can safely treat diabetes by the selective inhibition of PTP1B. In addition, if neuronal PTP1B is inhibited rapid weight loss can be induced in obese individuals thus also treating the effects of obesity, prevent neurodegeneration or Alzheimer's. A drug of this type would also be useful for the treatment of complications due to obesity, obesity in type II diabetes, high serum cholesterol, sleep apnea (especially in pickwickian syndrome), nonalcoholic steatohepatitis and surgery for obese patients. Finally, a PTP1B inhibitor could also be useful for the treatment of cancer.

SUMMARY OF THE INVENTION

The present invention relates to various aminosteroids which inhibit protein phosphatase IB (PTPIB). The invention also relates to compositions which contain these aminosteroids, and methods of their use to treat diabetes in mammals, particularly humans.

One aspect of the invention relates to steroid compounds that are inhibitors of the enzyme PTP1B of the following formula, or a pharmaceutically acceptable salt thereof:

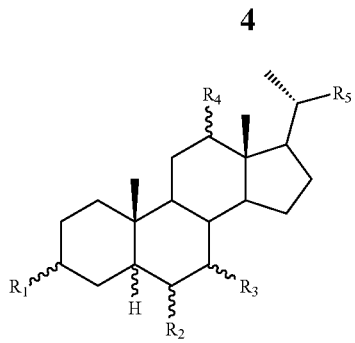

wherein:
$R_1$=—NH(CH$_2$)$_{1-4}$—NH—$R_6$ or —OH or =O or H or piperazine or amino piperidine;
$R_6$=—(CH$_2$)$_{1-4}$—NH—$R_7$ or $C_1$-$C_5$ alkyl or phenyl or H;
$R_7$=—(CH$_2$)$_{1-4}$—N—$R_8$;
$R_8$=$C_1$-$C_5$ alkyl or benzyl or benzyl with 1-3 $R_9$ groups or H;
$R_9$=—OH or —OCH$_3$ or —$C_1$-$C_5$ alkyl;
$R_2$=—OH or H;
$R_3$=—OH or H;
$R_4$=—OH or H;

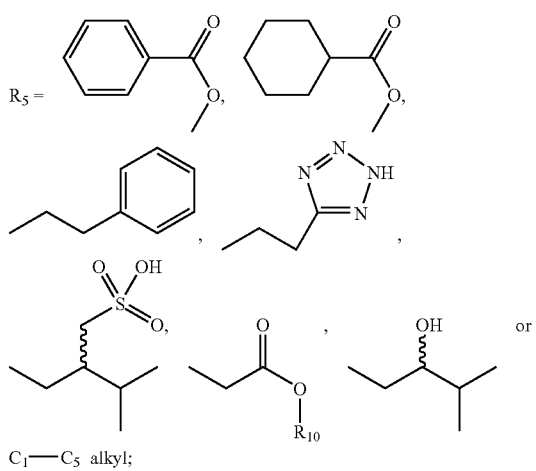

$R_{10}$=H or $C_1$-$C_5$ alkyl.

Another aspect of the invention is a compound selected from the compounds listed in Table 1, or a pharmaceutically acceptable salt thereof.

Another aspect of the invention is a pharmaceutical composition comprising a compound listed in Table 1 and a diluent or carrier.

Another aspect of the invention is a method of treating or preventing diabetes in a mammal, particularly a human, comprising administering to said mammal a therapeutically effective amount of a compound of the above formula or a compound listed in Table 1.

Another aspect of the invention is a method for treating a disorder in a mammal mediated by inhibition of protein tyrosine phosphatase PTP1B comprising administering to a mammal in need thereof a therapeutically effective amount of a compound of the above formula or a compound of Table 1.

In exemplary embodiments, the disorder treated by administration of a compound of the above formula or a compound of Table 1 includes, but is not limited to, obesity in type II diabetes, high serum cholesterol, sleep apnea and nonalcoholic steatohepatitis.

DETAILED DESCRIPTION OF THE INVENTION

Figure 1:
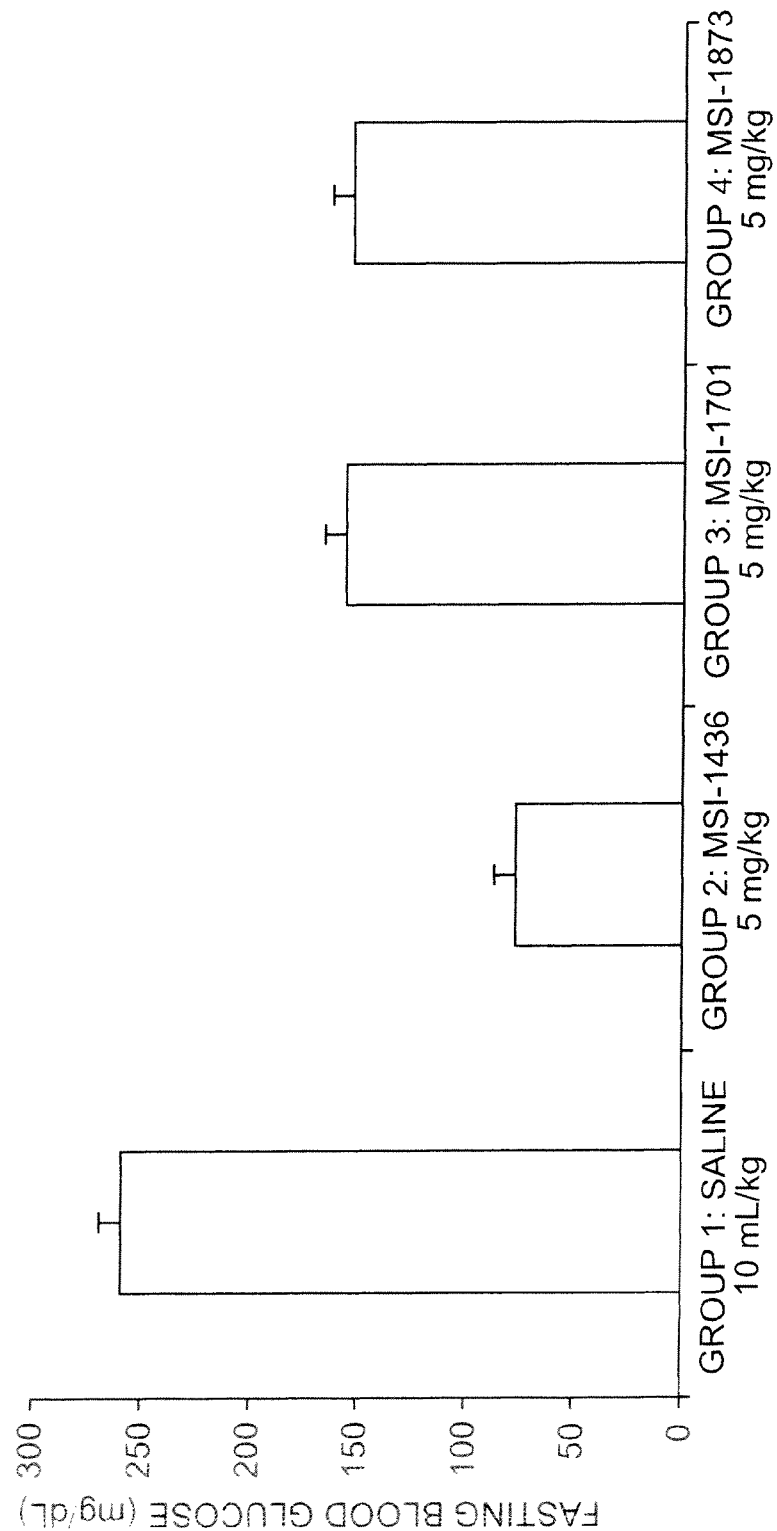
FIG. 1 shows that MSI-1701 and 1873 treated ob/ob mice have lower fasting blood glucose levels compared to saline treated controls.

The compounds listed in Table 1 are intended to include all pharmaceutically acceptable salts of the listed compounds. In addition, where the stereochemistry at any given carbon atom is undefined, it is intended that each individual stereoisomer is encompassed as well as the racemic mixture.

The aminosteroids of the invention may be administered alone or as part of a pharmaceutical composition. Pharmaceutical compositions for use in vitro or in vivo in accordance with the present invention may be formulated in a conventional manner using one or more physiologically acceptable carriers comprising excipients and auxiliaries that facilitate processing of the active compounds into preparations which can be used pharmaceutically. Proper formulation is dependent upon the route of administration chosen. Examples of carriers or excipients include, but are not limited to, calcium carbonate, calcium phosphate, various sugars, starches, cellulose derivatives, gelatin and polymers such as polyethylene glycols.

In addition to carriers, the pharmaceutical compositions of the invention may also optionally include stabilizers, preservatives and/or adjuvants. For examples of typical carriers, stabilizers and adjuvants known to those of skill in the art, see *Remington: The Science and Practice of Pharmacy*, Lippincott, Williams & Wilkins, $21^{st}$ ed. (2005), which is incorporated by reference in its entirety.

Optionally, other therapies known to those of skill in the art may be combined with the administration of the aminosteroids of the invention. More than one aminosteroid may be present in a single composition.

In vivo administration of the aminosteroids of the invention can be effected in one dose, multiple doses, continuously or intermittently throughout the course of treatment. Doses range from about 0.01 mg/kg to about 10 mg/kg, preferably between about 0.01 g/kg to about 1 mg/kg, and most preferably between about 0.1 mg/kg to about 1 mg/kg in single or divided daily doses. Methods of determining the most effective means and dosages of administration are well known to those of skill in the art and will vary with the composition used for therapy, the purpose of the therapy, the target cell being treated and the subject being treated. Single or multiple administrations can be carried out with the dose level and pattern being selected by the treating physician.

Pharmaceutical compositions containing the aminosteroids of the invention can be administered by any suitable route, including oral, rectal, intranasal, topical (including transdermal, aerosol, ocular, buccal and sublingual), parenteral (including subcutaneous, intramuscular, intravenous), intraperitoneal and pulmonary. It will be appreciated that the preferred route will vary with the condition and age of the recipient, and the disease being treated.

For oral administration, the aminosteroids of the invention can be formulated readily by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as maize starch, wheat starch, rice starch, potato starch, gelatin, gum tragacanth, methyl cellulose, hydroxypropylmethylcellulose, sodium carboxymethylcellulose and polyvinylpyrrolidone (PVP). If desired, disintegrating agents may be added, such as the cross-linked polyvinyl pyrrolidone, agar, alginic acid or a salt thereof; such as sodium alginate.

For administration by inhalation, the aminosteroids of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The aminosteroids can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as buffers, bacteriostats, suspending agents, stabilizing agents, thickening agents, dispersing agents or mixtures thereof.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides or liposomes. Aqueous injection suspensions may contain substances that increase the viscosity of the suspension, such as sodium carboxymethyl cellulose, sorbitol or dextran. Optionally, the suspension may also contain suitable stabilizers or agents that increase the solubility of the compounds to allow for the preparation of highly concentrated solutions. In a preferred embodiment, the aminosteroids of the invention are dissolved in a 5% sugar solution, such as dextrose, before being administered parenterally.

For injection, the aminosteroids of the invention may be formulated in aqueous solutions, preferably in physiologically compatible buffers such as Hanks's solution, Ringer's solution or physiological saline buffer. For transmucosal administration, penetrants appropriate to the barrier to be permeated are used in the formulation. Such penetrants are generally known in the art.

The aminosteroids may also be formulated in rectal compositions such as suppositories or retention enemas, e.g., containing conventional suppository bases such as cocoa butter or other glycerides.

The aminosteroids may also be combined with at least one additional therapeutic agent.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Inhibition of PTP1B by Steroid Analogues

The steroid analogues were tested for inhibition against the commercially available full length tyrosine phosphatase PTP1B. The ability of each analogue to inhibit the activity of PTP1B was measured in the presence of 10 µM of the steroid analogue. The assay uses para-nitro-phenyl phosphate (pNPP), a non-specific substrate to assess phosphatase activity. Phosphatase activity was based on the ability of PTP 1B to catalyze the hydrolysis of pNPP to p-nitrophenol (pNP). The activity was measured using a single point spectrophometric absorbance at 405 nm (the absorbance of the chromogenic product, para-nitrophenol (pNP). The percent inhibition of tyrosine phosphatase activity by the steroid analogues was determined by the fractional response of pNP formation in the presence of inhibitor over the maximal response pNP formation observed in the absence of inhibitor. The results of these assays are shown in Table 1, column C and show many analogues that cause greater than 50% inhibition at 5 µM concentration.

Example 2

Inhibition of TCPTP by Steroid Analogues

The steroid analogues were also tested for their ability to inhibit the tyrosine phosphatase TCPTP as an indication of their potential toxicity by the inhibition of the immune response. The TCPTP inhibition assay was done in the same manner as the PTP1B assay except full length TCPTP was used as the enzyme and the inhibitor was at a concentration of 200 µM. The results of the TCPTP inhibition assays are shown in Table 1, column D and show three compounds that inhibit TCPTP less than 50% even at a 20 fold greater concentration.

Example 3

Effect of Steroid Analogues on Body Weight, Blood Glucose Levels and The Oral Glucose Tolerance Test (OGTT) in the Diabetic Mouse To determine in vivo efficacy of the steroid analogues a Db/db (Lepr$^{db}$) in mouse model was used. Db/db mice are extensively used for screening of antidiabetic agents. Db/db mice were treated with either saline or 5 or 10 mg/kg steroid analogue every 3 days for a total of 4 doses via ip injection. Body weight, glucose tolerance and fasting blood glucose levels were measured for each group during the study. Each group had at least an N of 4 animals. All reagents and lab animals are commercially available.

Starting at study day 0, body weight measurements were taken every day for each group for up to 30 days. Percent change in body weight was calculated as the fractional response of body weight on study day X over the original body weight on study day 0. Animals displaying a reduction in body weight suggest that the steroid analogue inhibits neuronal PTP1B as is shown for MSI-1436 in Example 4 below. Table 1, column G shows % change in body weight for some 1436 analogues. MSI-1431 is seen to produce weight loss similar to 1436 but 1701 and 1873 able to inhibit PTP1B but do not produce weight loss.

On study day 13, all animal groups were fasted overnight. On study day 14, 25 µL of whole blood was collected and analyzed for the glucose level (mg/dL) using a glucose analyzer. A significant reduction of FBG levels compared to saline control is shown for MSI-1431, 1436, 1701, 1814 and 1873 in FIG. 1 and Table 1, column D.

Figure 2:
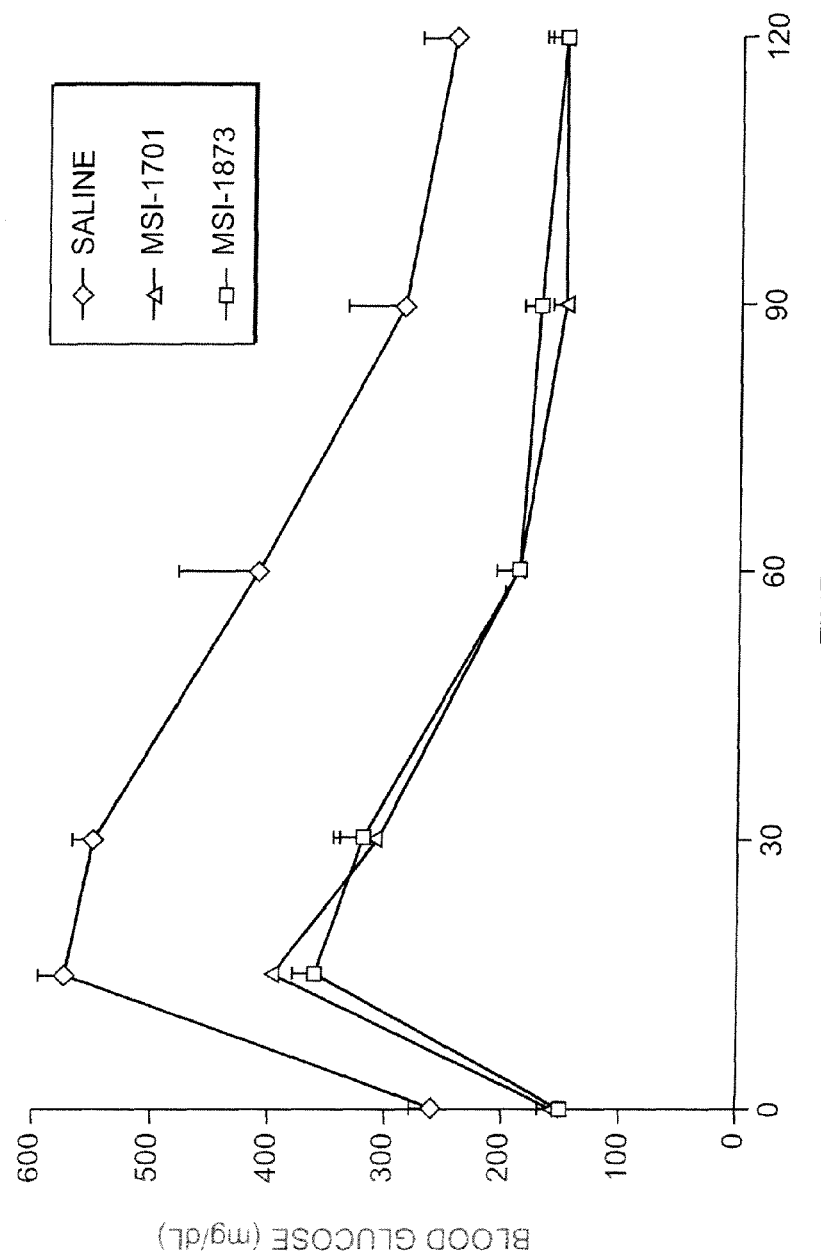
FIG. 2 shows a graph of the glucose tolerance test that produced the data in FIG. 3.
Figure 3:
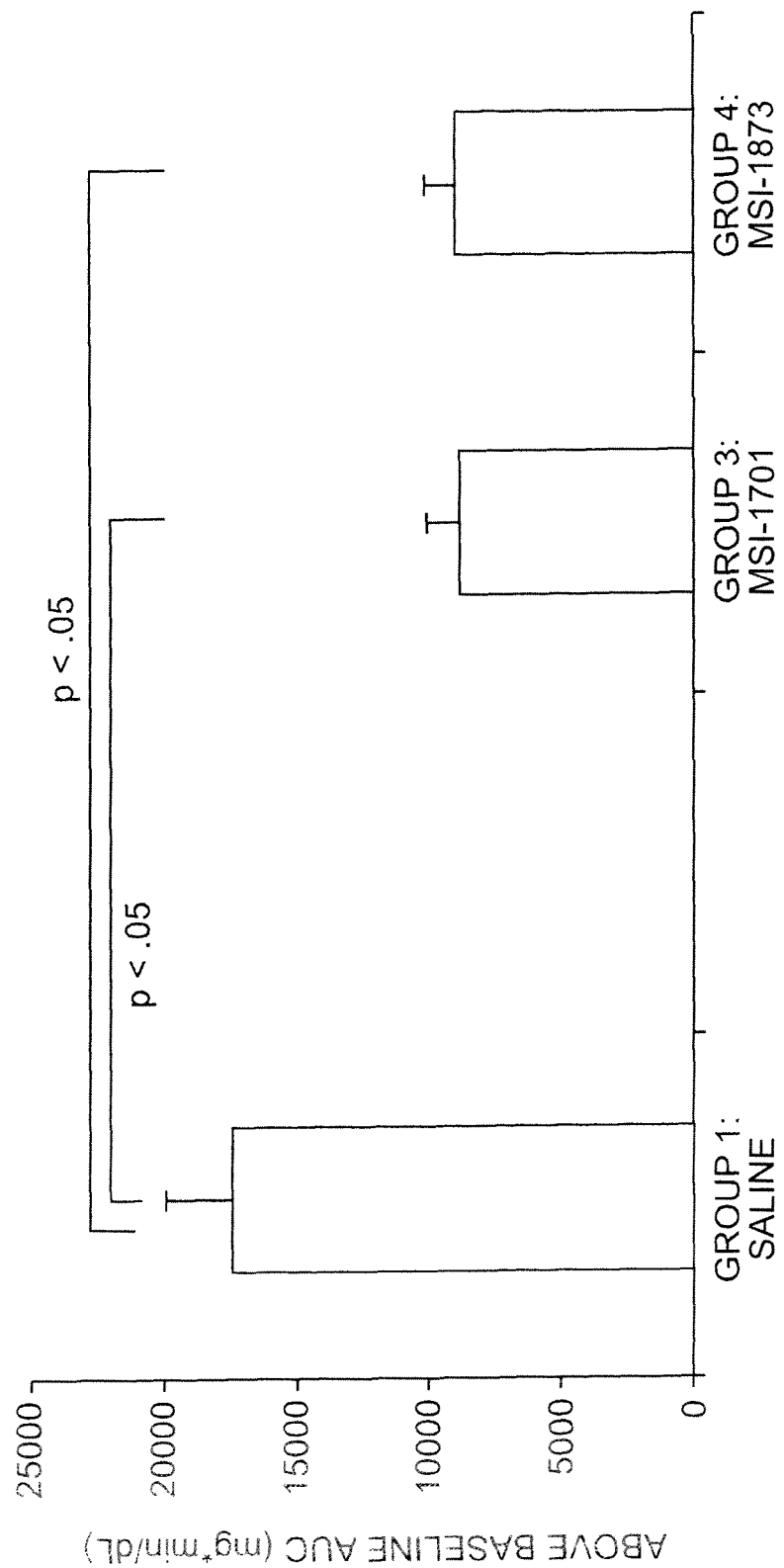
FIG. 3 shows that MSI-1701 and 1873 treated ob/ob mice respond significantly faster in a glucose tolerance test than the saline treated controls.

Also on study day 14, an OGTT was performed to assess glucose tolerance. At time 0, an oral glucose challenge (1.5 g/kg) was administered by oral gavage. At timepoints 0, 15, 30, 60, 90, 120 min post glucose load, 25 µl of whole blood was withdrawn from the tail vein of the animal and the glucose level was measured using a glucose analyzer. The glucose concentration vs time was plotted (FIG. 2). Above baseline area under the curve (ABAUC) of the glucose excursion time curve was determined using trapezoidal rule analyses. A significant reduction ($p<0.05$) in ABAUC compared to saline control is shown for MSI-1431, 1436, 1701, 1814 and 1873 in FIG. 3 and Table 1, column F.

Example 4

Effect of MSI-1436 on the Phosphorylation of IR-β in the Rat hypothalamus

Male SD rats were divided into 8 groups with 4 rats per group. All rats were fed ad libitum normal rodent chow and regular tap water. On Day 0, rats were dosed via intraperitoneal (i.p.) injection with 10 mg/kg MSI-1436 or 0.9% saline. Rats were fasted overnight from Day 0 to Day 1. On Day 1, animals were dosed i.p. with 0.9% saline or 100 U/kg of insulin. At 15 or 30 minutes post-dose (Day 1), animals were sacrificed and the hypothalamuses were harvested, transferred to 1.5 mL eppendorf tubes, and frozen in liquid nitrogen. Samples were stored at −80° C. until further analysis. Hypothalamuses were pooled (3-4 per group) and homogenized in 2-mL Wheaton vials and Dounce homogenizers in 1 mL of tissue extraction reagent plus phosphatase and protease inhibitors. Lysates were centrifuged for 10 minutes at 4° C. (14,000 rpm) and the supernatants were transferred to new 1.5 mL eppendorf tubes. Lysates (500 µg) were immunoprecipitated for Insulin Receptor β overnight at 4° C. The samples were then bound to Protein A according to standard protocols for 4 hours at 4° C. Samples were then washed 4× with RIPA/Empigen buffer and eluted in 4×LDS sample buffer. After elution, the samples were boiled at 95° C. for 5 min.

Figure 4:
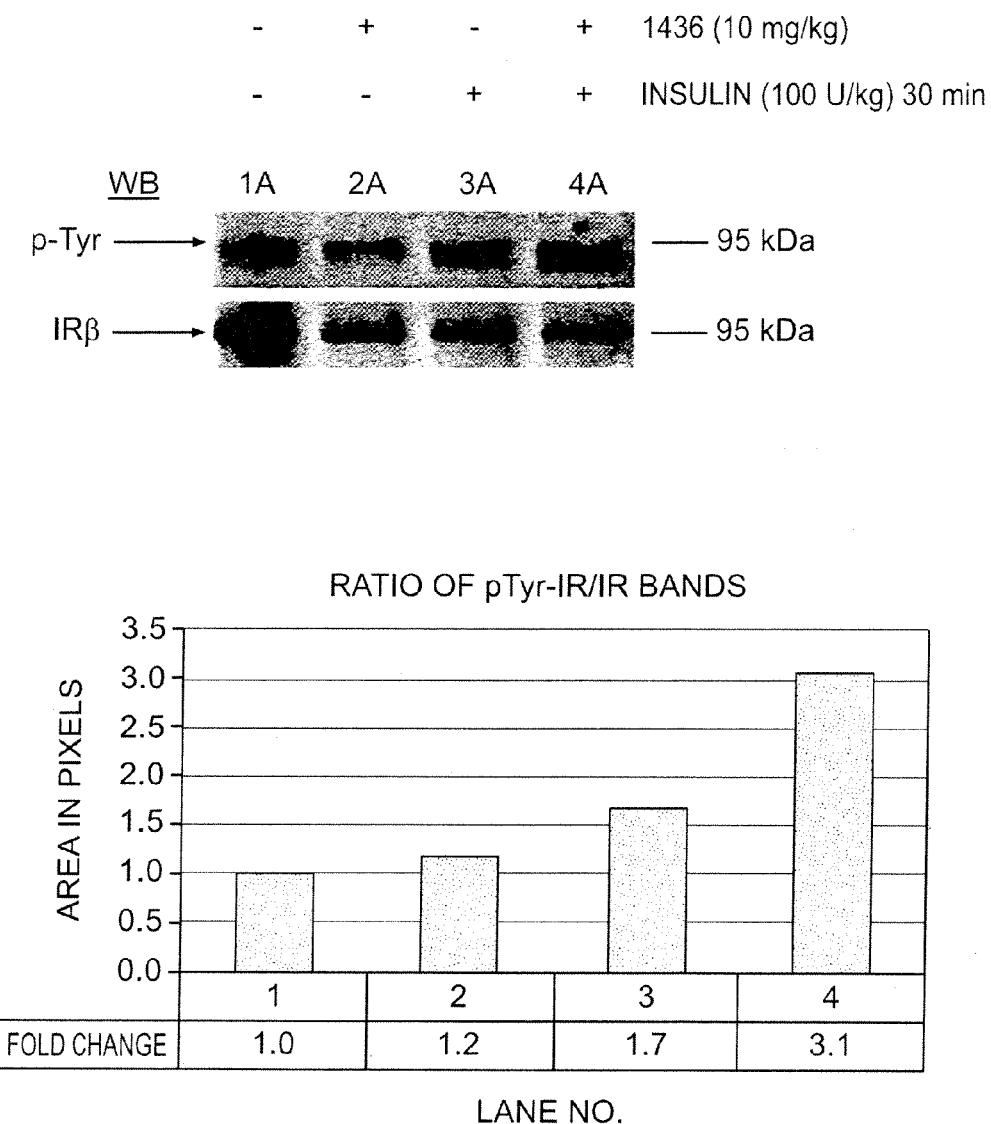
FIG. 4 shows that MSI-1436 can increase the level of insulin stimulated tyrosine phosphoralation of 1143 in the rat hypothalamus.

500 µg of total protein from each sample was loaded onto a 1.5 mm 4-12% Bis-Tris Novex gel and run at 175V for approximately 1 hr in 1×MOPS buffer. The gel was transferred to nitrocellulose membrane overnight at 4° C. and 10V in a Novex transfer blot apparatus and blocked the following morning in 5% BSA for 1 hr at room temperature. Next, the membrane was incubated in anti-pTyr 4G10 primary antibody diluted to 1 µg/µL in 1% BSA at room temperature for 2 hours. After 3 ten-minute washes in TBST, the membrane was incubated at room temperature in goat anti-mouse secondary antibody diluted 1:80,000 in 1% BSA for 1 hr. Finally, the membrane was washed 3×10 min in TBST, 5×2 min in pico pure water, and developed using SuperSignal West Pico ECL reagent. The membrane was exposed to film for various time points. Densitometric analysis of the bands of interest was performed using ImageJ. The ratio of the pTyr-IRβ band to the IRβ band was computed in Excel and the fold change in IR phosphorylation determined. The data indicates (FIG. 4) that treatment with MSI-1436 nearly doubles the amount of phospho-Tyrosine found on insulin stimulated IR-β in the hypothalamus. The assumption in this case is that MSI-1436 has crossed the blood brain barrier into the hypothalamus and increased the amount of phosphor-Tyrosine on IR-β by the inhibition on PTP1B.

TABLE 1

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1241 | 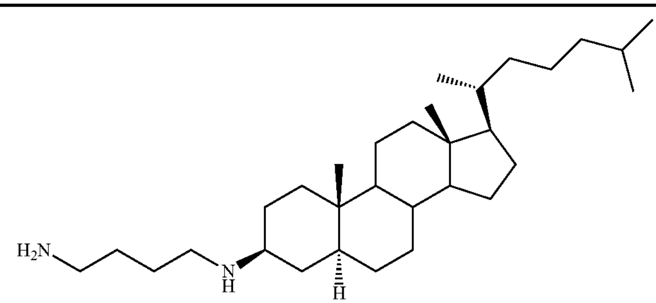 | 22 | | | | |
| 1255 | 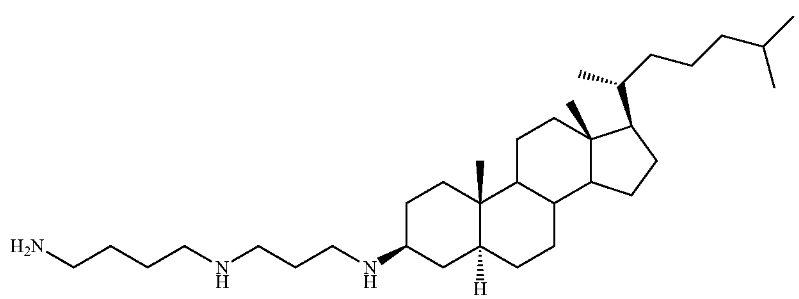 [SMILES: CC(C)CCC[C@@H](C)[C@H]1CCC2C3CC[C@H]4C[C@@H](NCCCNCCCCN)CC[C@]4(C)C3CC[C@@]21C] | 43 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1256 | 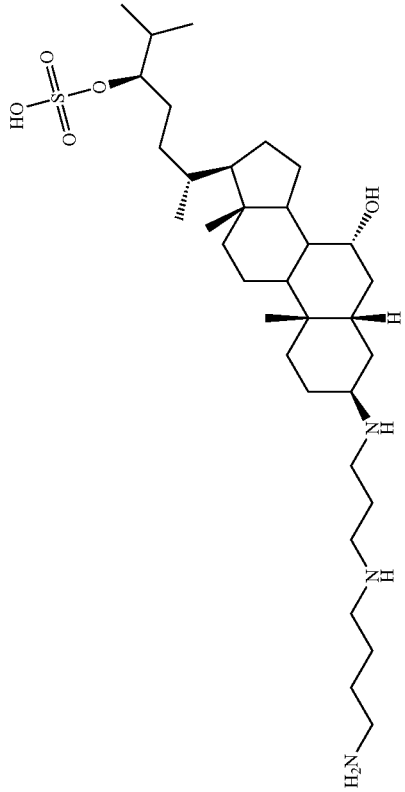 | 24 | | | | |
| 1271 | 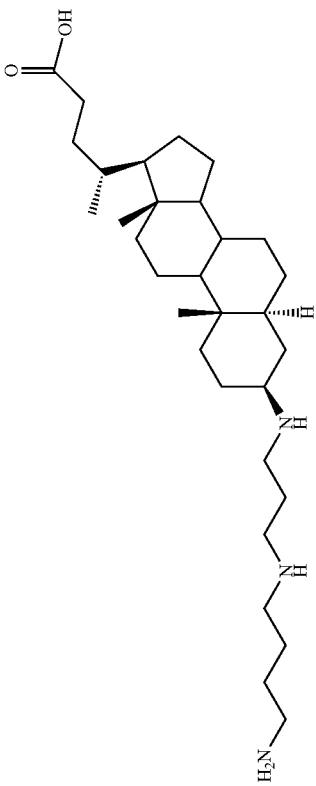 | 26 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1272 | 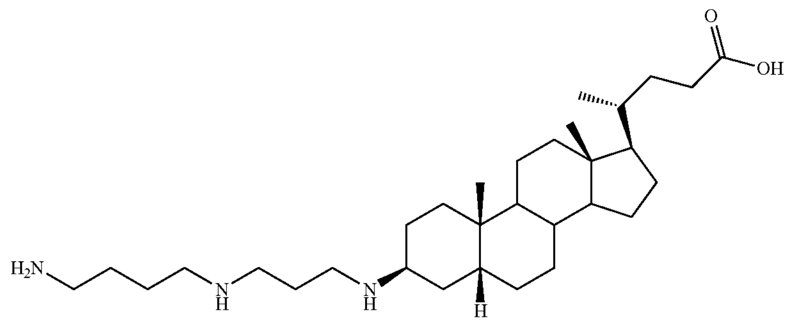 [SMILES: C[C@H](CCC(=O)O)[C@H]1CCC2C3CC[C@@H]4C[C@@H](NCCCNCCCCN)CC[C@]4(C)C3CC[C@@]21C] | 23 | | | | |
| 1303 | 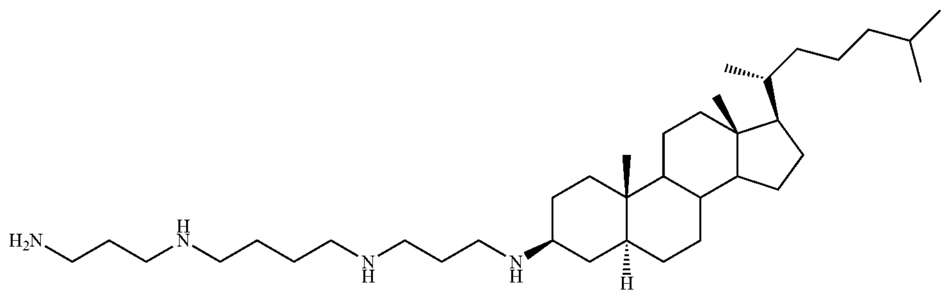 [SMILES: CC(C)CCC[C@@H](C)[C@H]1CCC2C3CC[C@H]4C[C@@H](NCCCNCCCCNCCCN)CC[C@]4(C)C3CC[C@@]21C] | 58 | 83 | | | |
| 1304 | 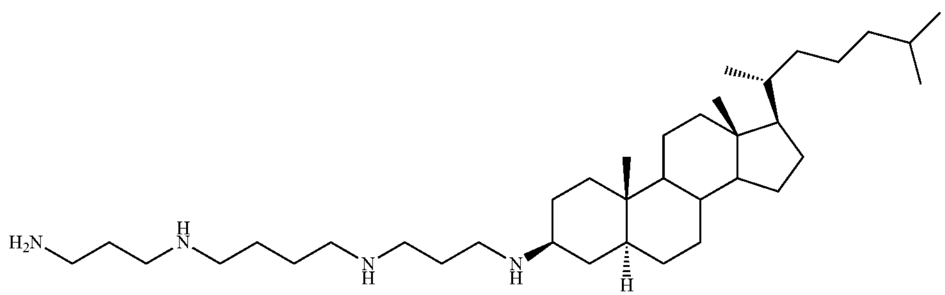 [SMILES: CC(C)CCC[C@@H](C)[C@H]1CCC2C3CC[C@H]4C[C@@H](NCCCNCCCCNCCCN)CC[C@]4(C)C3CC[C@@]21C] | 71 | | | | |

TABLE 1-continued
| Compound | Structure | PTP1B Inhibition (5 µM) | TCPTP Inhibition (200 µM) | % Reduction in FBG | % Reduction in OGTT Above Baseline AUC | % Change in Body Weight |
|---|---|---|---|---|---|---|
| 1317 | 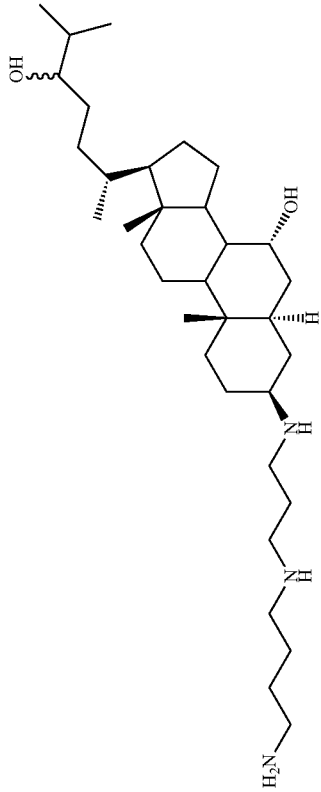 | 43 | | | | |
| 1320 | 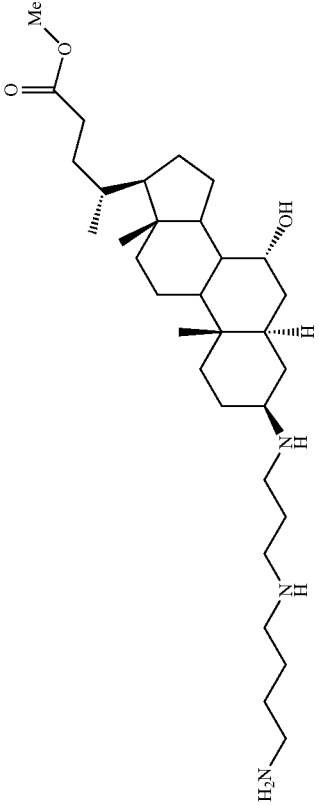 | 48 | 0 | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1321 | (steroid structure with carboxylic acid and diamine chain) | 28 | | | | |
| 1322 | (steroid structure with carboxylic acid and diamine chain) | 16 | | | | |

TABLE 1-continued

| Compound | Structure | PTP1B Inhibition (5 µM) | TCPTP Inhibition (200 µM) | % Reduction in FBG | % Reduction in OGTT Above Baseline AUC | % Change in Body Weight |
|---|---|---|---|---|---|---|
| 1336 | 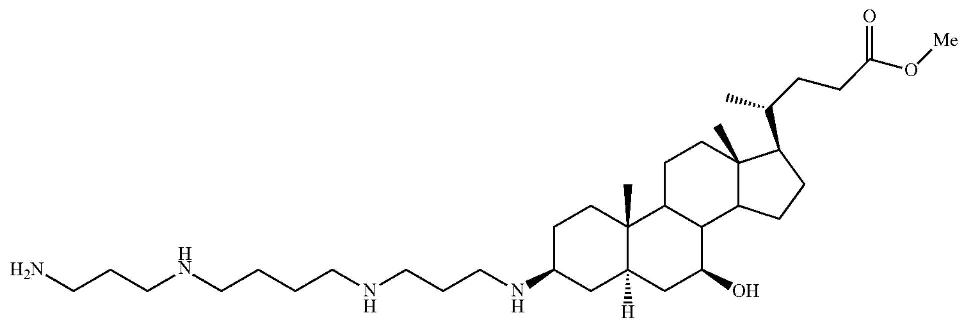 [SMILES: COC(=O)CC[C@@H](C)[C@H]1CCC2C3C(CC[C@@]21C)[C@@]1(C)CC[C@H](NCCCNCCCCNCCCN)C[C@@H]1C[C@@H]3O] | 67 | | | | |
| 1352 | 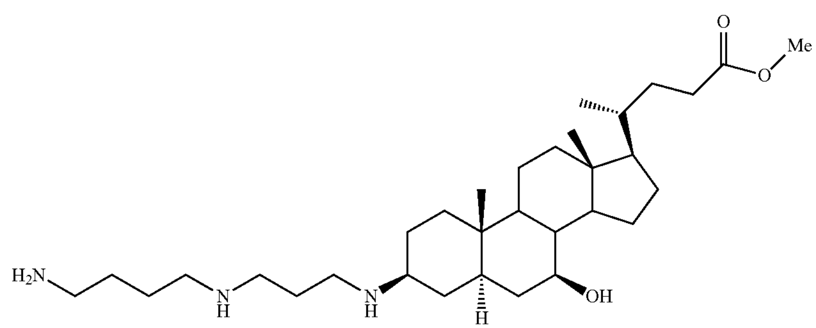 [SMILES: COC(=O)CC[C@@H](C)[C@H]1CCC2C3C(CC[C@@]21C)[C@@]1(C)CC[C@H](NCCCNCCCCN)C[C@@H]1C[C@@H]3O] | 38 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1370 | 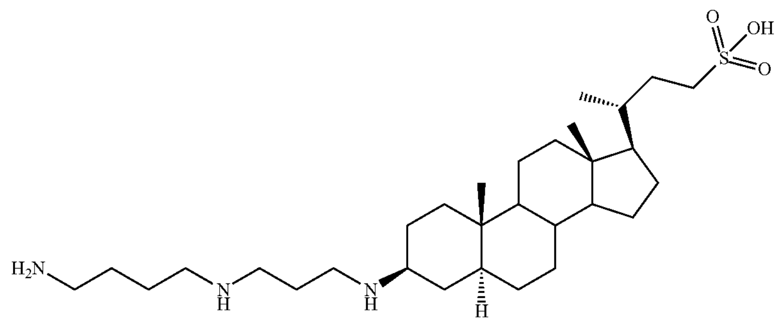 [SMILES: C[C@H](CCS(=O)(=O)O)[C@H]1CCC2C3CC[C@H]4C[C@@H](NCCCNCCCCN)CC[C@]4(C)C3CC[C@@]21C] | 66 | 44 | | | |
| 1371 | 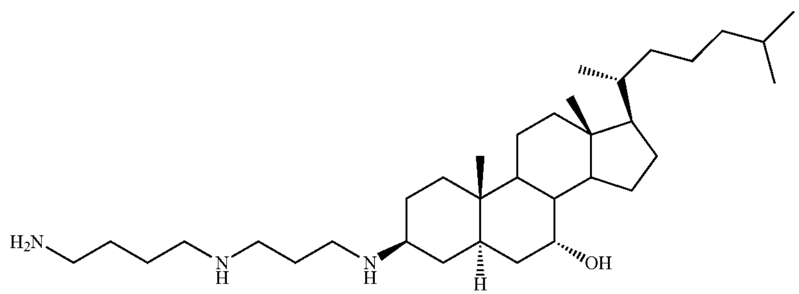 [SMILES: CC(C)CCC[C@@H](C)[C@H]1CCC2C3C(CC[C@@]21C)[C@@]1(C)CC[C@H](NCCCNCCCCN)C[C@@H]1C[C@H]3O] | 90 | 0 | | | |
| 1409 | 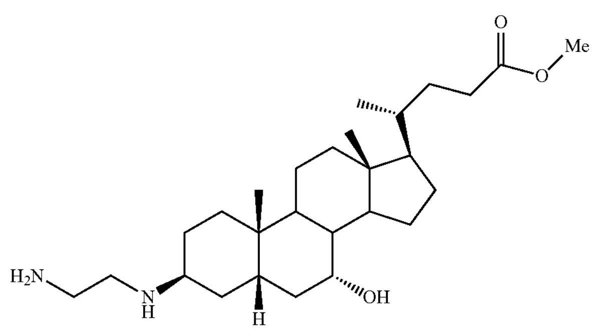 [SMILES: COC(=O)CC[C@@H](C)[C@H]1CCC2C3C(CC[C@@]21C)[C@@]1(C)CC[C@H](NCCN)C[C@H]1C[C@H]3O] | 7 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1413 | 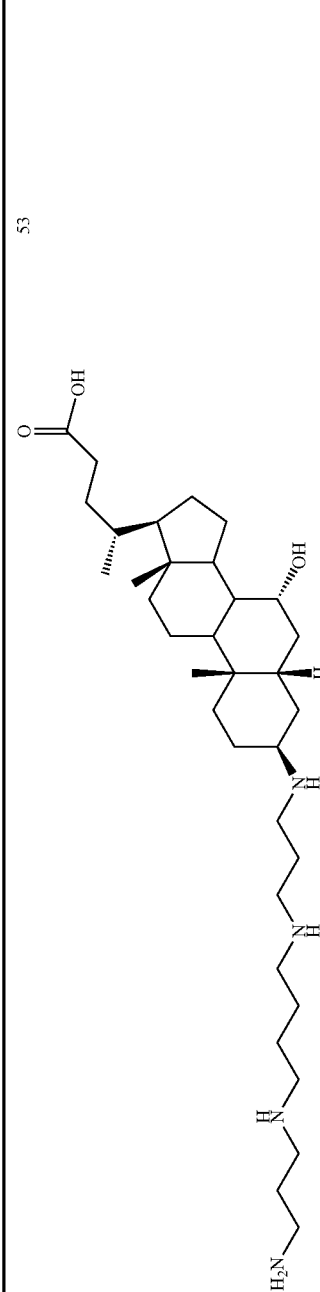 | 53 | | | | |
| 1431 | 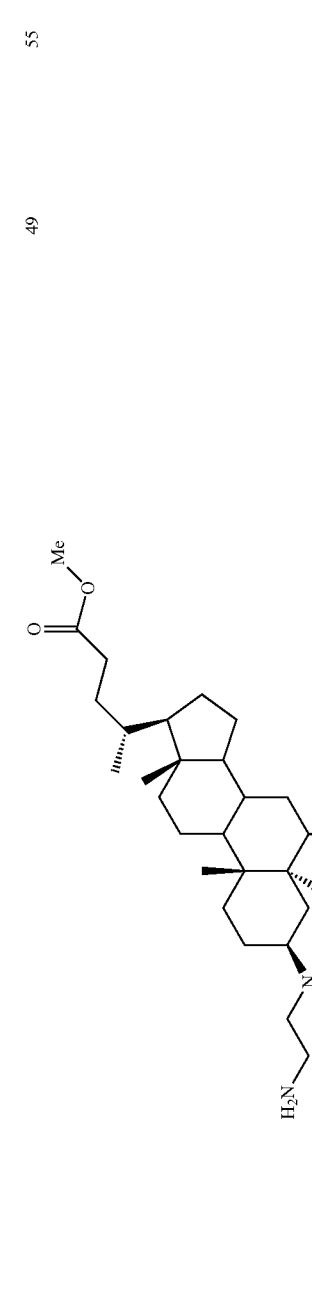 | 49 | | 55 | 47 | −7 |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1432 | 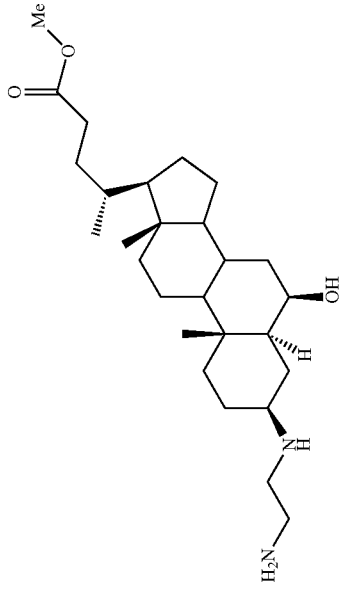 | 22 | | | | |
| 1436 | 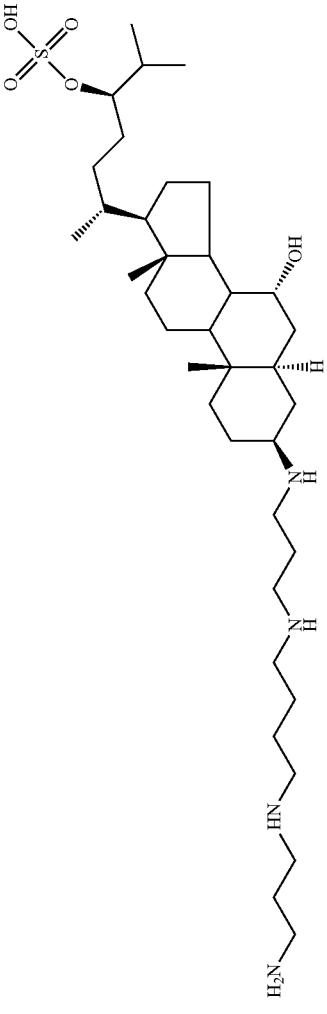 | 72 | 0 | 64 | 83 | −8 |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1433 | (structure) | 27 | | | | |
| 1437 | (structure) | 40 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1448 | 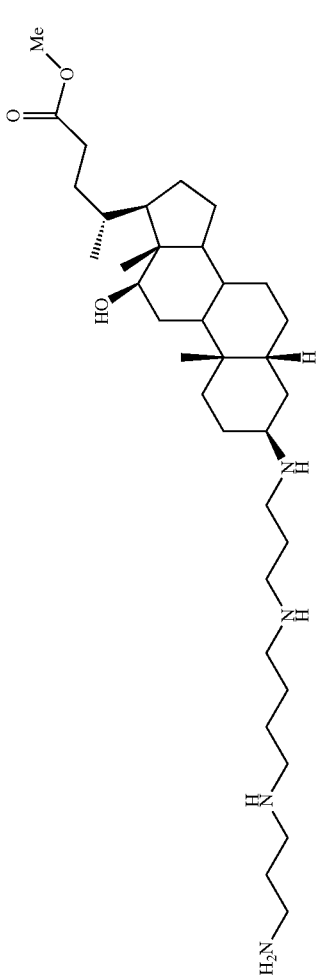 | 65 | | | | |
| 1459 | 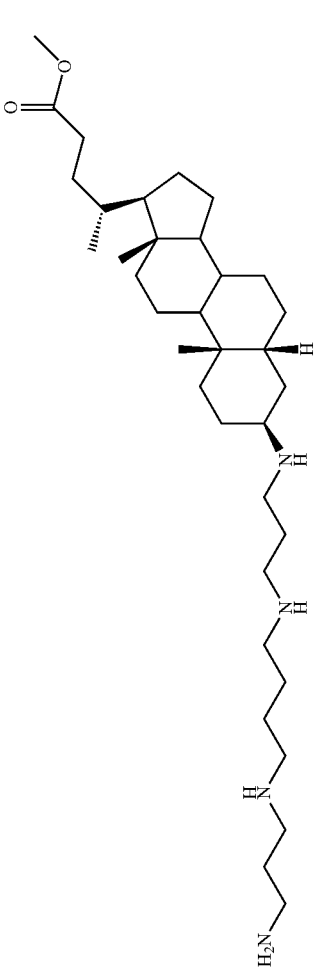 | 75 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1466 | 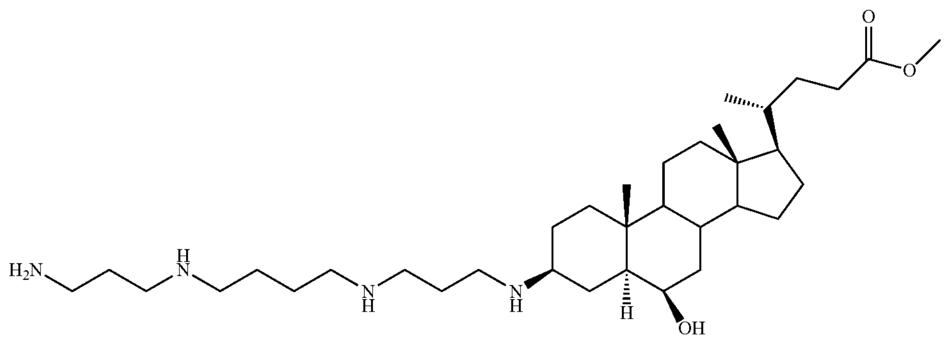 [SMILES: COC(=O)CC[C@@H](C)[C@H]1CCC2C3C[C@@H](O)[C@H]4C[C@@H](NCCCNCCCCNCCCN)CC[C@]4(C)C3CC[C@@]21C] | 85 | | | | |
| 1469 | 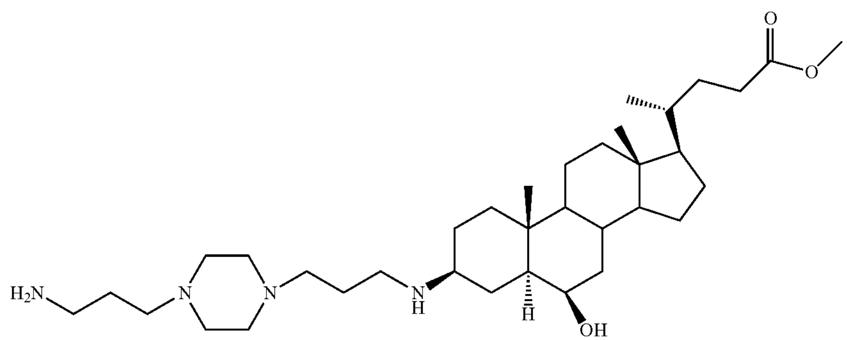 [SMILES: COC(=O)CC[C@@H](C)[C@H]1CCC2C3C[C@@H](O)[C@H]4C[C@@H](NCCCN5CCN(CCCN)CC5)CC[C@]4(C)C3CC[C@@]21C] | 85 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1470 | 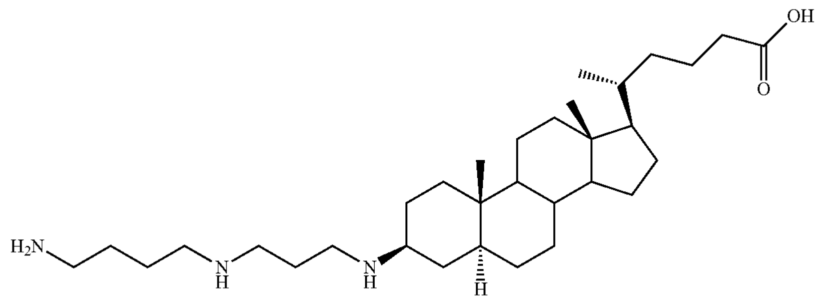 [SMILES: C[C@H](CCCC(=O)O)[C@H]1CCC2C3CC[C@H]4C[C@@H](NCCCNCCCCN)CC[C@]4(C)C3CC[C@@]21C] | 59 | | | | |
| 1486 | 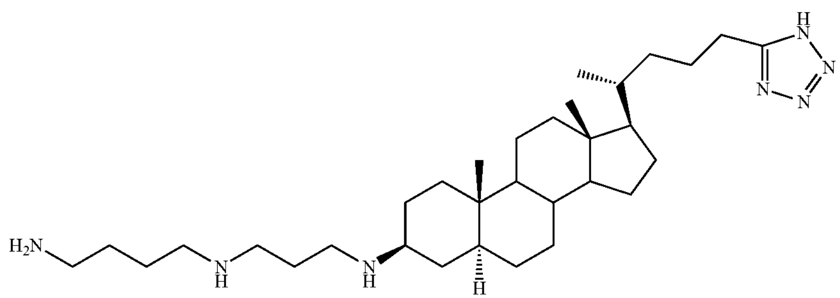 [SMILES: C[C@H](CCCc1nnn[nH]1)[C@H]1CCC2C3CC[C@H]4C[C@@H](NCCCNCCCCN)CC[C@]4(C)C3CC[C@@]21C] | 25 | | | | |
| 1487 | 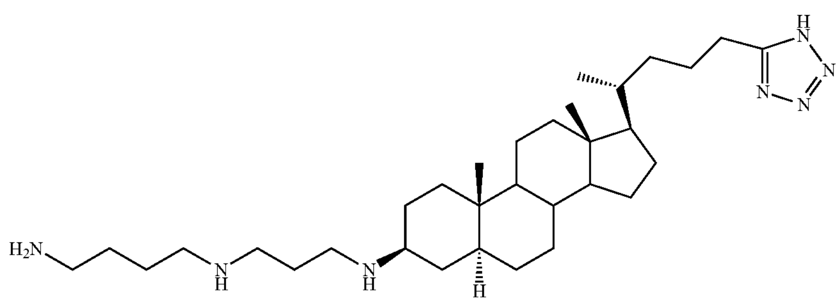 [SMILES: C[C@H](CCCc1nnn[nH]1)[C@H]1CCC2C3CC[C@H]4C[C@@H](NCCCNCCCCN)CC[C@]4(C)C3CC[C@@]21C] | 44 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1520 | 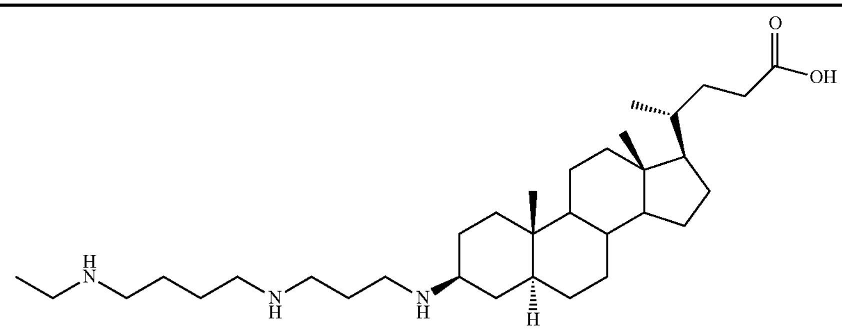 | 31 | | | | |
| 1521 | 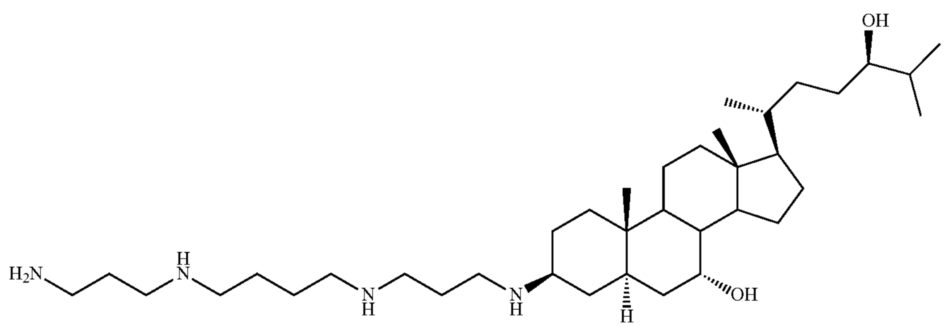 [SMILES: CC(C)[C@H](O)CC[C@@H](C)[C@H]1CCC2C3C(CC[C@@]21C)[C@@]1(C)CC[C@H](NCCCNCCCCNCCCN)C[C@@H]1C[C@H]3O] | 50 | | | | |
| 1561 | 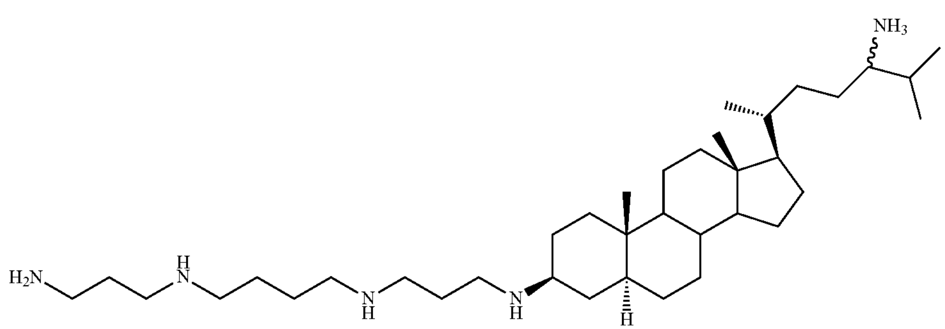 | 13 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1562 | 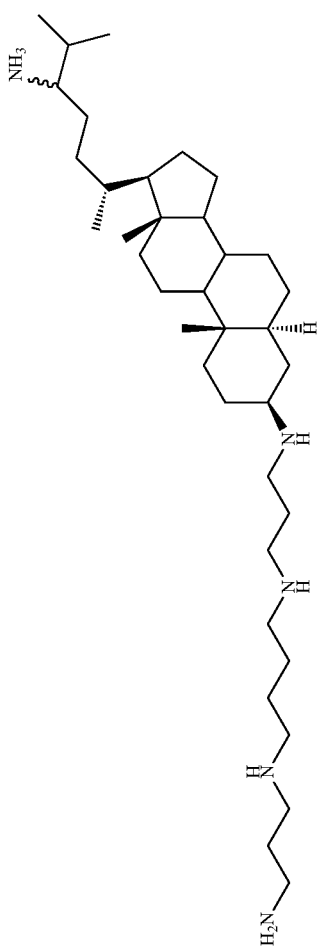 | 20 | | | | |
| 1569 | 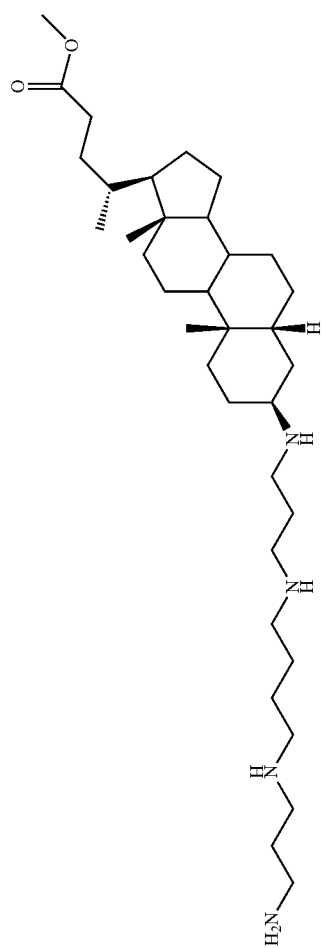 | 46 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1597 | 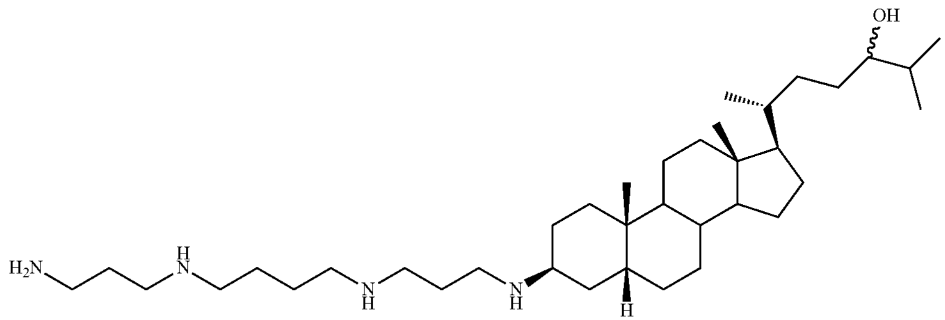 [SMILES: CC(C)C(O)CC[C@@H](C)[C@H]1CCC2C3CC[C@@H]4C[C@@H](NCCCNCCCCNCCCN)CC[C@]4(C)C3CC[C@@]21C] | 70 | | | | |
| 1598 | 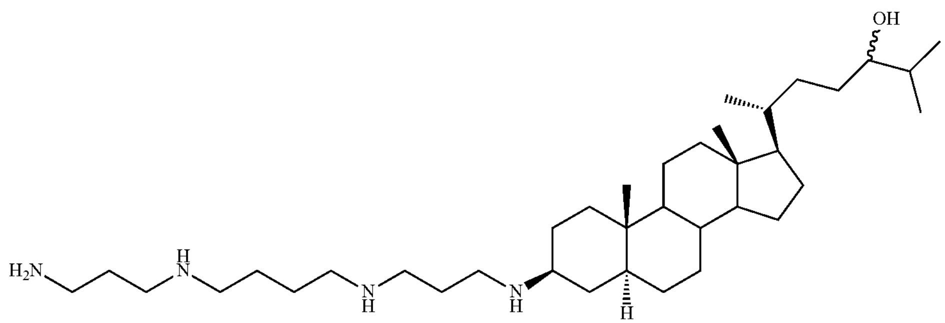 [SMILES: CC(C)C(O)CC[C@@H](C)[C@H]1CCC2C3CC[C@H]4C[C@@H](NCCCNCCCCNCCCN)CC[C@]4(C)C3CC[C@@]21C] | 68 | | | | |
| 1678 | 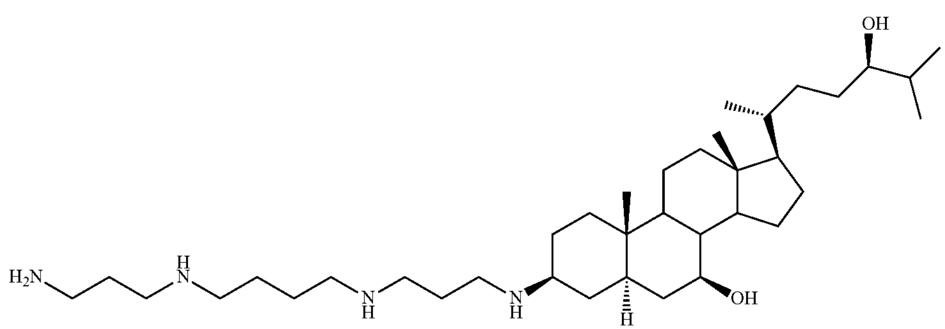 [SMILES: CC(C)[C@H](O)CC[C@@H](C)[C@H]1CCC2C3C(CC[C@@]21C)[C@@]1(C)CC[C@H](NCCCNCCCCNCCCN)C[C@@H]1C[C@@H]3O] | 22 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1701 | 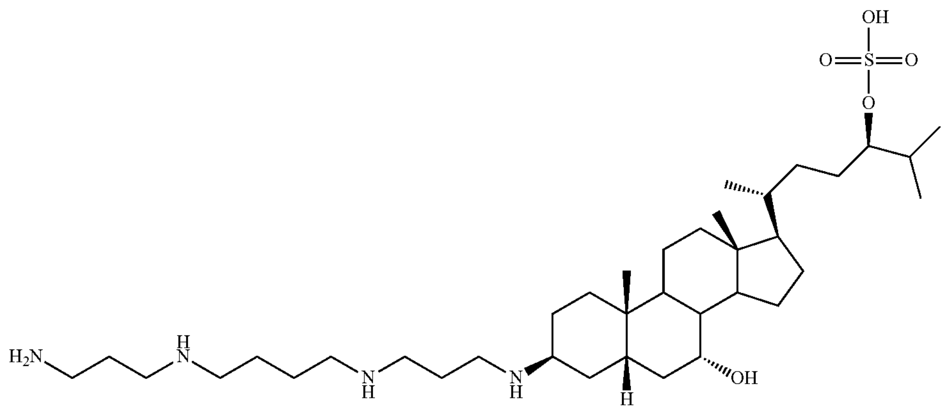 [SMILES: CC(C)[C@@H](CC[C@@H](C)[C@H]1CCC2C3C(CC[C@@]21C)[C@@]1(C)CC[C@H](NCCCNCCCCNCCCN)C[C@H]1C[C@H]3O)OS(=O)(=O)O] | 41 | | 40 | 49 | 3 |
| 1718 | 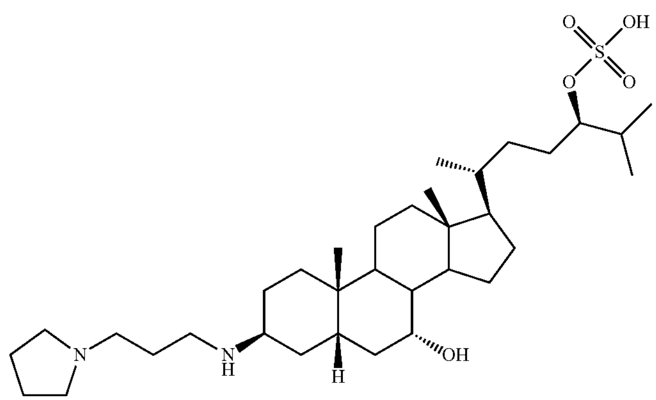 [SMILES: CC(C)[C@@H](CC[C@@H](C)[C@H]1CCC2C3C(CC[C@@]21C)[C@@]1(C)CC[C@H](NCCCN2CCCC2)C[C@H]1C[C@H]3O)OS(=O)(=O)O] | 19 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1751 | 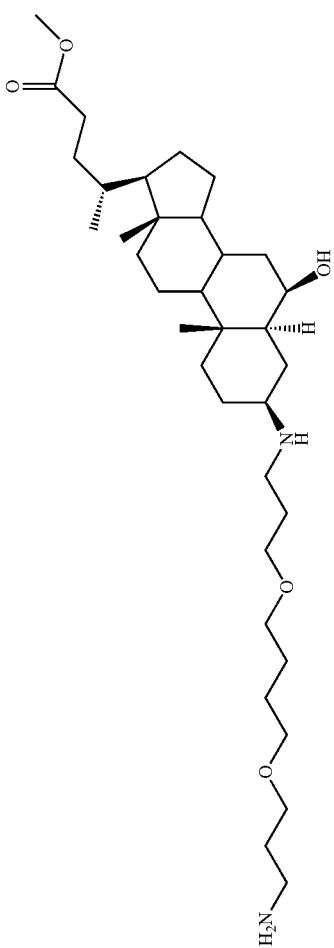 | 6 | | | | |
| 1755 | 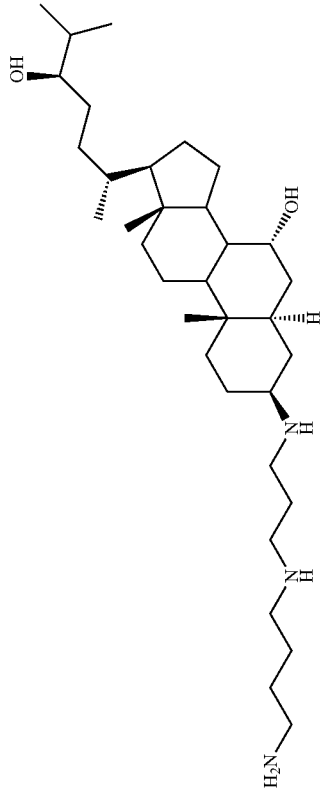 | 24 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1768 | (structure) | 13 | | | | |
| 1777 | (structure) | 37 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1783 | 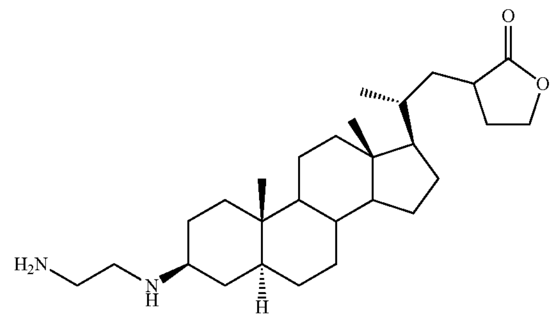 [SMILES: C[C@H](CC1CCOC1=O)[C@H]1CCC2C3CC[C@H]4C[C@@H](NCCN)CC[C@]4(C)C3CC[C@@]21C] | 36 | | | | |
| 1804 | 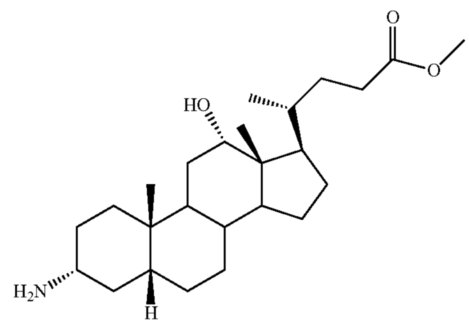 [SMILES: COC(=O)CC[C@@H](C)[C@H]1CCC2C3CC[C@@H]4C[C@H](N)CC[C@]4(C)C3C[C@H](O)[C@@]21C] | 10 | | | | |
| 1805 | 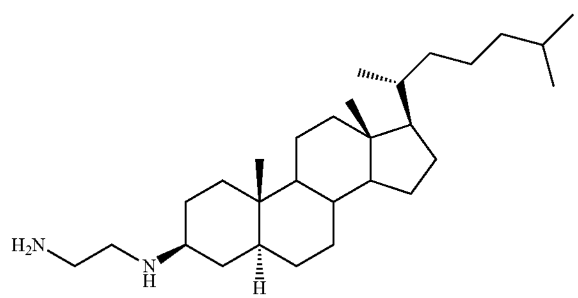 [SMILES: CC(C)CCC[C@@H](C)[C@H]1CCC2C3CC[C@H]4C[C@@H](NCCN)CC[C@]4(C)C3CC[C@@]21C] | 17 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1810 | 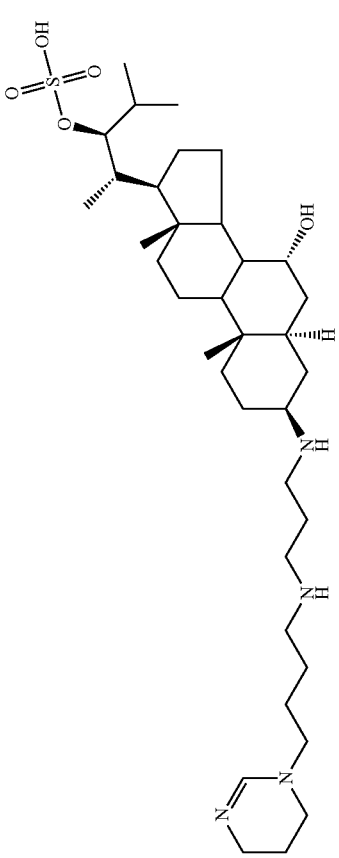 | 30 | | | | |
| 1811 | 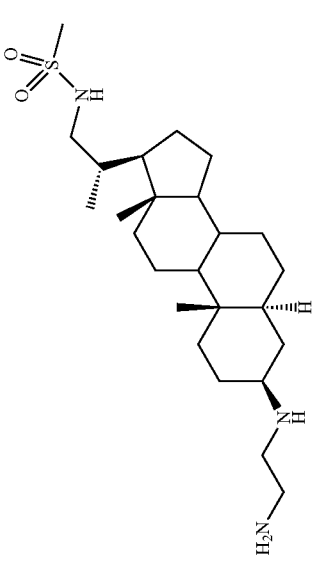 | 8 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1812 | 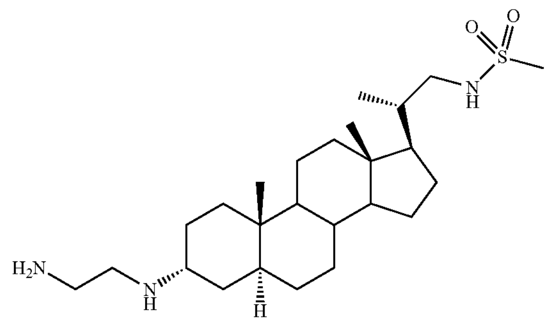 [SMILES: C[C@H](CNS(C)(=O)=O)[C@H]1CCC2C3CC[C@H]4C[C@H](NCCN)CC[C@]4(C)C3CC[C@@]21C] | 37 | | | | |
| 1814 | 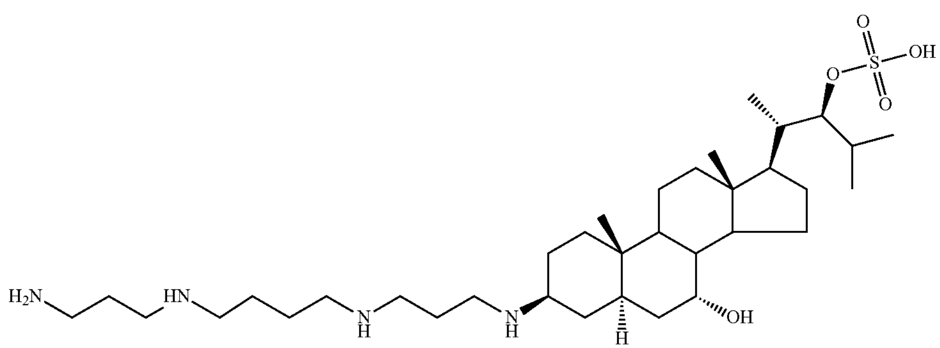 [SMILES: CC(C)[C@H](OS(=O)(=O)O)[C@@H](C)[C@H]1CCC2C3C(CC[C@@]21C)[C@@]1(C)CC[C@H](NCCCNCCCCNCCCN)C[C@@H]1C[C@H]3O] | 58 | | 46 | 60 | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1830 | 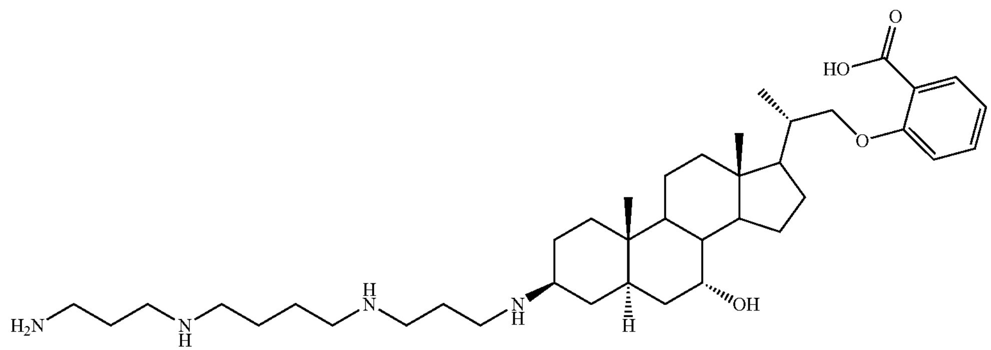 [SMILES: C[C@H](COc1ccccc1C(=O)O)C1CCC2C3C(CC[C@@]21C)[C@@]1(C)CC[C@H](NCCCNCCCCNCCCN)C[C@@H]1C[C@H]3O] | 18 | | | | |
| 1839 | 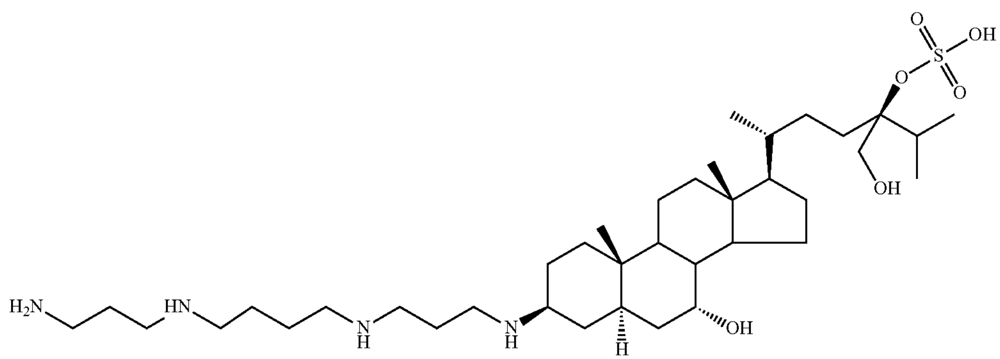 [SMILES: CC(C)[C@](CO)(CC[C@@H](C)[C@H]1CCC2C3C(CC[C@@]21C)[C@@]1(C)CC[C@H](NCCCNCCCCNCCCN)C[C@@H]1C[C@H]3O)OS(=O)(=O)O] | 27 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1873 | 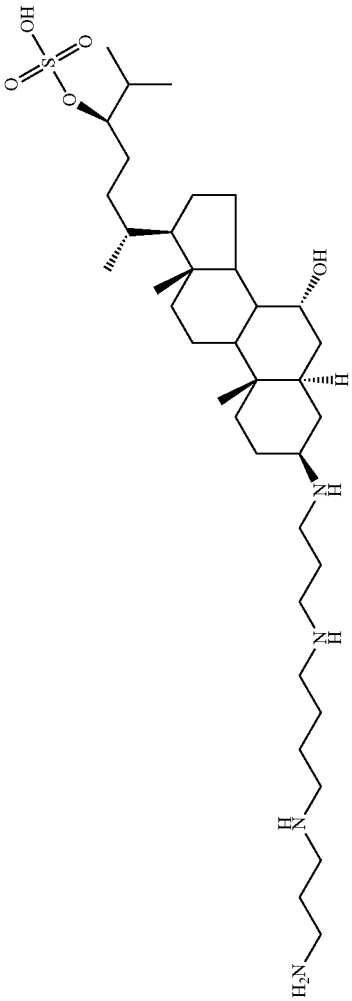 | 63 | | 41 | 47 | 4 |
| 1875 | 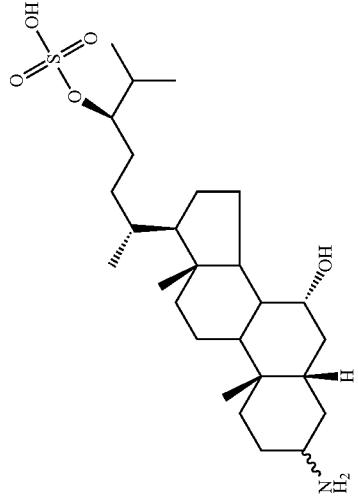 | 71 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1876 | 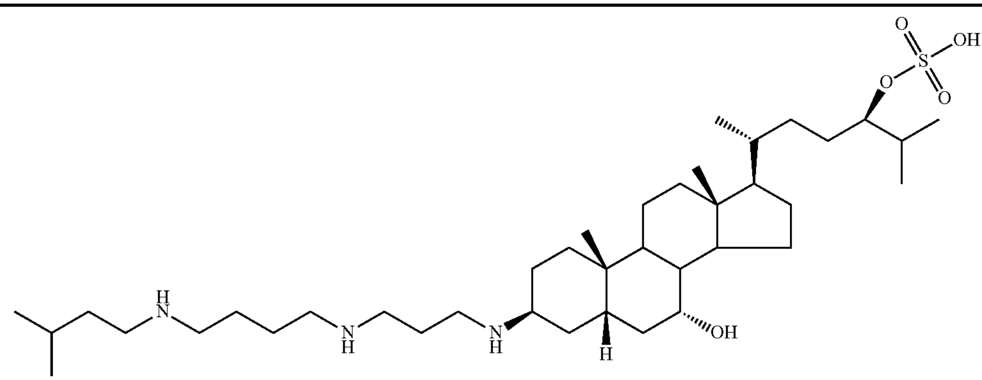 | 43 | | | | |
| 1877 | 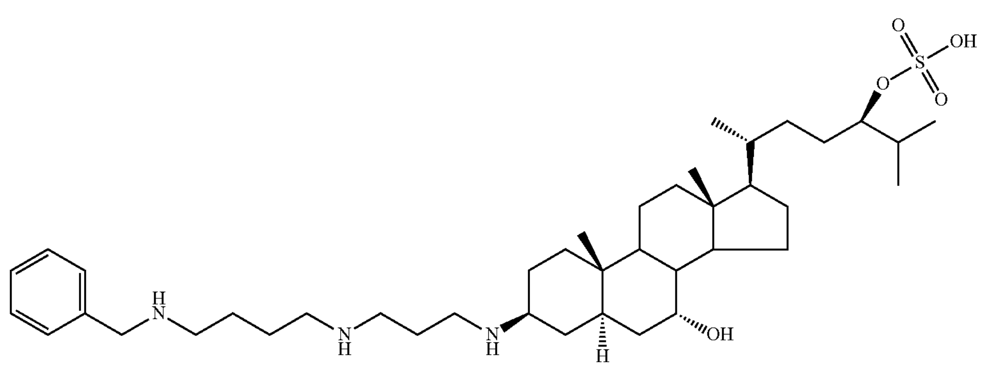 [SMILES: CC(C)[C@@H](CC[C@@H](C)[C@H]1CCC2C3C(CC[C@@]21C)[C@@]1(C)CC[C@H](NCCCNCCCCNCc2ccccc2)C[C@@H]1C[C@H]3O)OS(=O)(=O)O] | 47 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1888 | 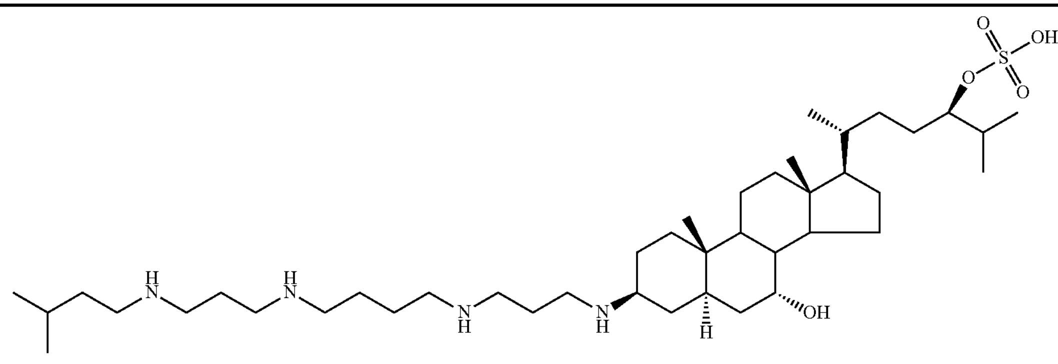 | 81 | | | | |
| 1892 | 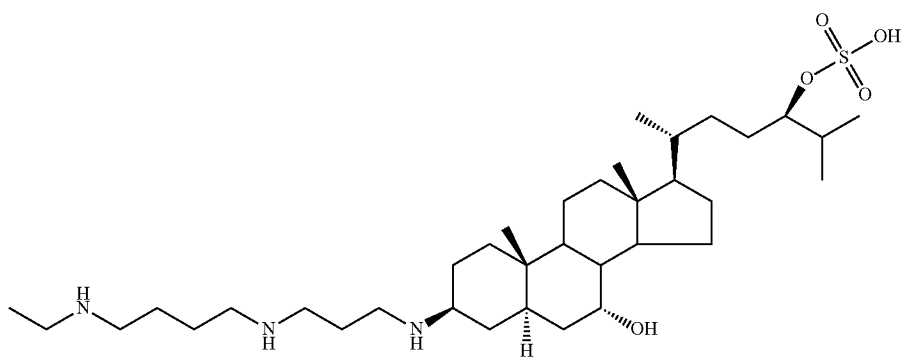 [SMILES: CCNCCCCNCCCN[C@H]1CC[C@]2(C)C3CC[C@@]4(C)C(CC[C@@H]4[C@H](C)CC[C@@H](OS(=O)(=O)O)C(C)C)C3[C@H](O)C[C@H]2C1] | 28 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1893 | 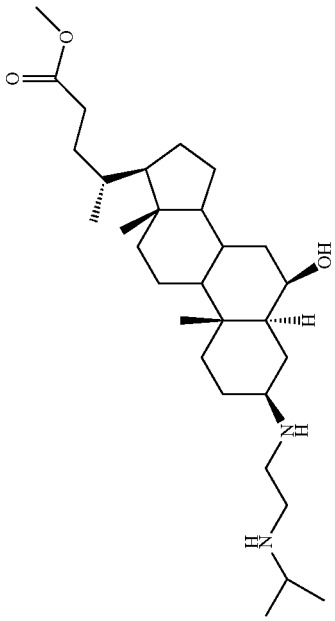 | 16 | | | | |
| 1894 | 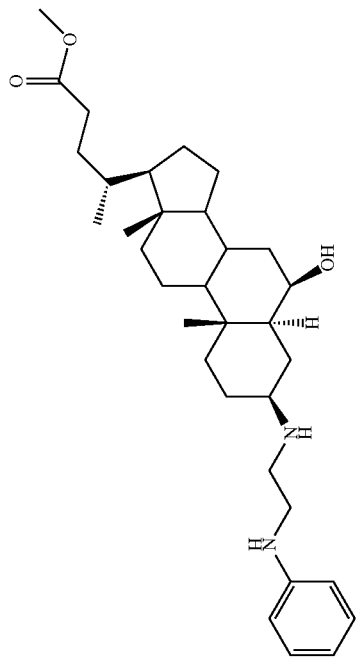 | 77 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1909 | 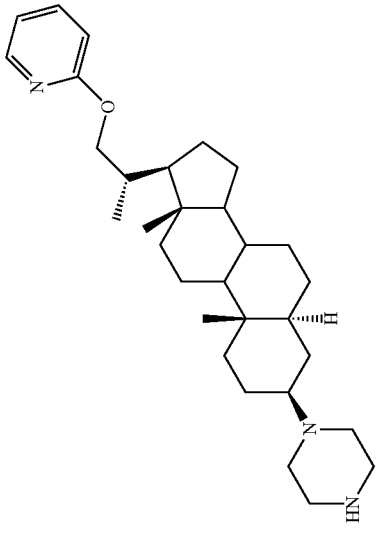 | 41 | | | | |
| 1911 | 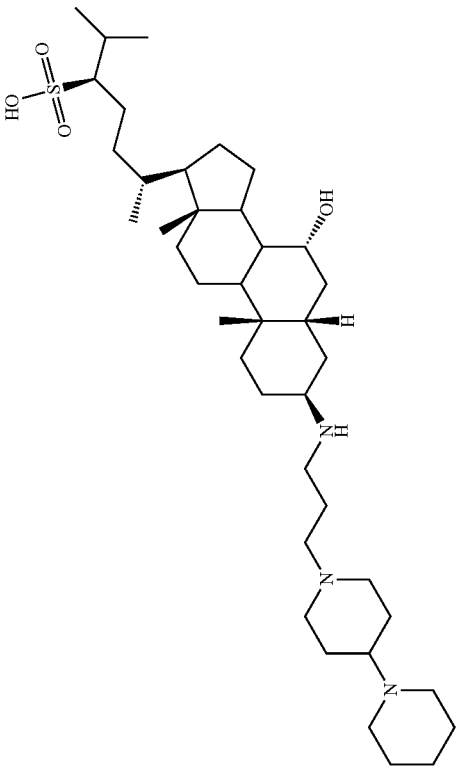 | 37 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 1913 | 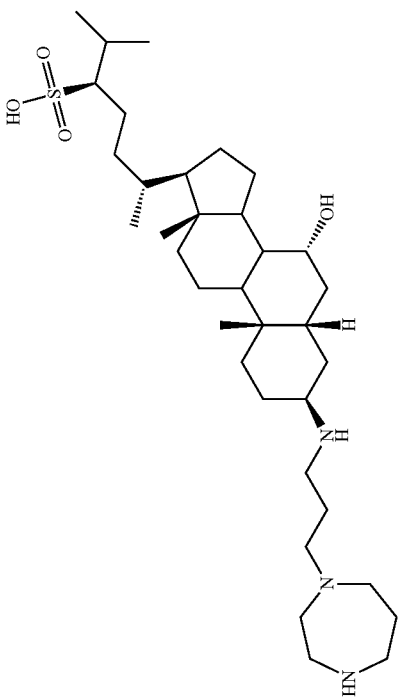 | 38 | | | | |
| 1920 | 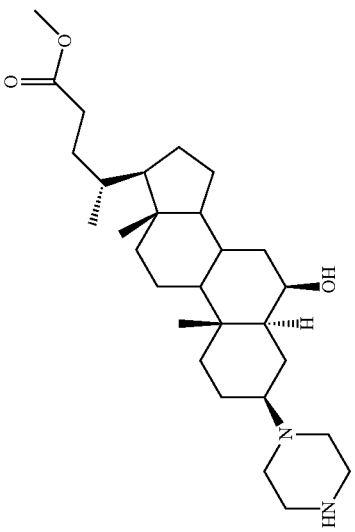 | 22 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2347 | 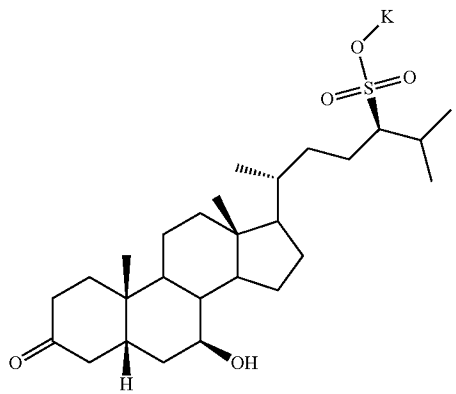 | 27 | | | | |
| 2348 | 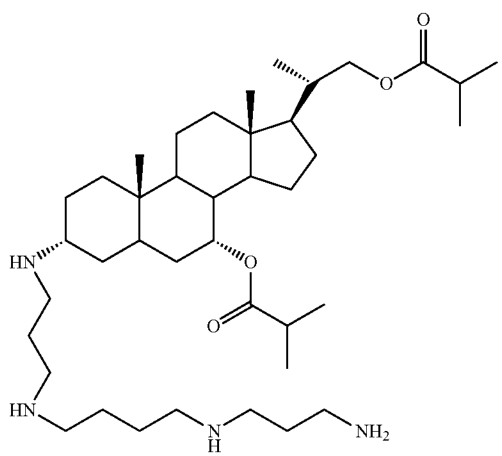 [SMILES: CC(C)C(=O)OC[C@@H](C)[C@H]1CCC2C3C(CC[C@@]21C)[C@@]1(C)CC[C@@H](NCCCNCCCCNCCCN)CC1C[C@H]3OC(=O)C(C)C] | 34 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2349 | 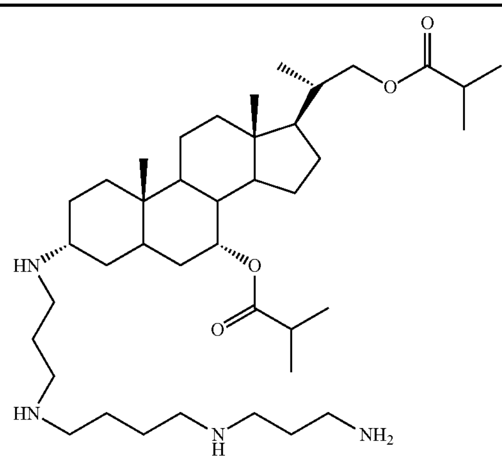 | 27 | | | | |
| 2351 | 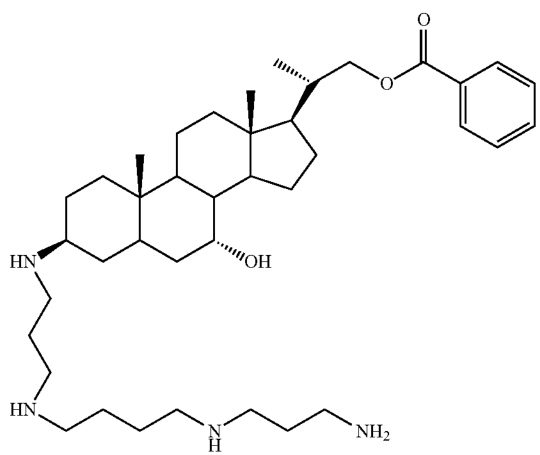 [SMILES: C[C@H](COC(=O)c1ccccc1)[C@H]1CCC2C3C(CC[C@@]21C)[C@@]1(C)CC[C@H](NCCCNCCCCNCCCN)CC1C[C@H]3O] | 88 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2352 | 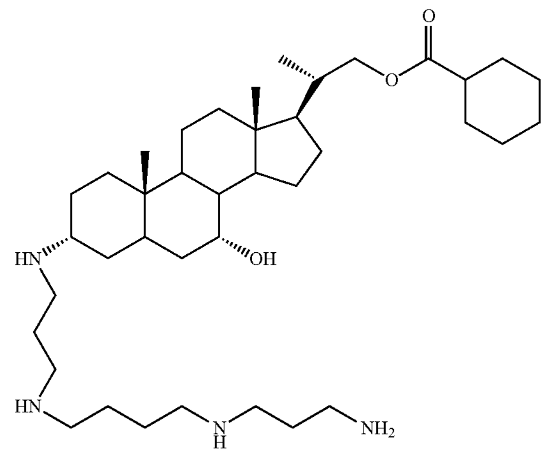 [SMILES: C[C@H](COC(=O)C1CCCCC1)[C@H]1CCC2C3C(CC[C@@]21C)[C@@]1(C)CC[C@@H](NCCCNCCCCNCCCN)CC1C[C@H]3O] | 76 | | | | |
| 2353 | 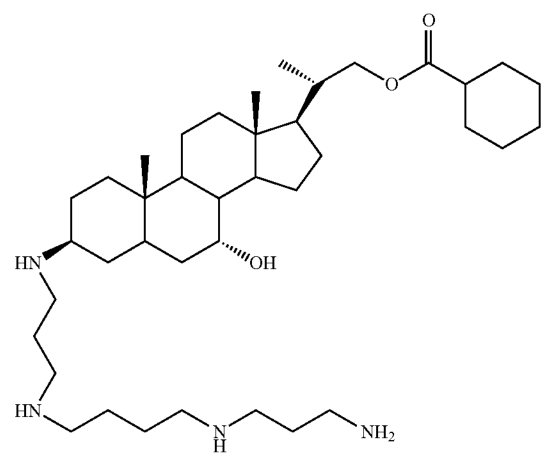 | 76 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2354 | 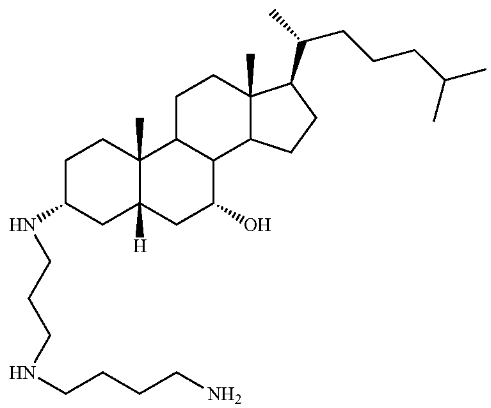 [SMILES: CC(C)CCC[C@@H](C)[C@H]1CCC2C3C(CC[C@@]21C)[C@@]1(C)CC[C@@H](NCCCNCCCCN)C[C@H]1C[C@H]3O] | 43 | | | | |
| 2355 | 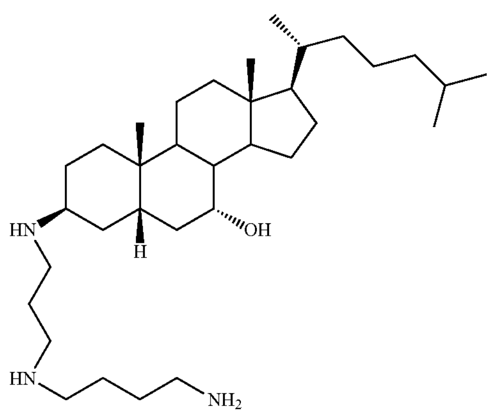 [SMILES: CC(C)CCC[C@@H](C)[C@H]1CCC2C3C(CC[C@@]21C)[C@@]1(C)CC[C@H](NCCCNCCCCN)C[C@H]1C[C@H]3O] | 35 | | | | |

TABLE 1-continued

| Compound | Structure | PTP1B Inhibition (5 µM) | TCPTP Inhibition (200 µM) | % Reduction in FBG | % Reduction in OGTT Above Baseline AUC | % Change in Body Weight |
|---|---|---|---|---|---|---|
| 2356 | 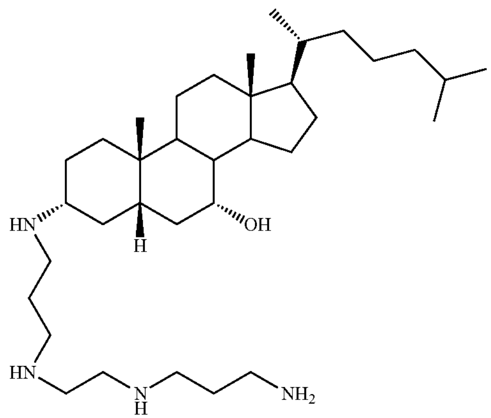 [SMILES: CC(C)CCC[C@@H](C)[C@H]1CCC2C3C(CC[C@@]21C)[C@@]1(C)CC[C@@H](NCCCNCCNCCCN)C[C@H]1C[C@H]3O] | 23 | | | | |
| 2357 | 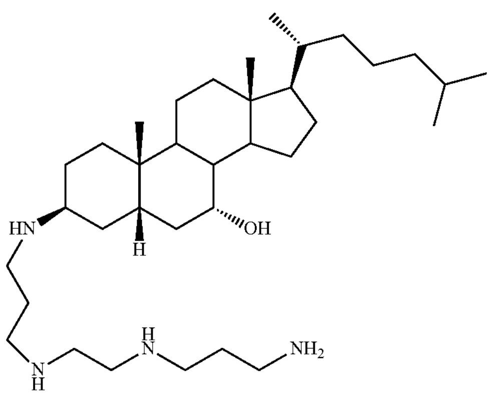 [SMILES: CC(C)CCC[C@@H](C)[C@H]1CCC2C3C(CC[C@@]21C)[C@@]1(C)CC[C@H](NCCCNCCNCCCN)C[C@H]1C[C@H]3O] | 29 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2358 | 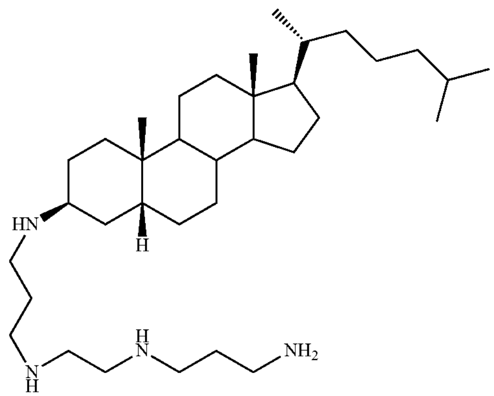 [SMILES: CC(C)CCC[C@@H](C)[C@H]1CCC2C3CC[C@@H]4C[C@@H](NCCCNCCNCCCN)CC[C@]4(C)C3CC[C@@]21C] | 24 | | | | |
| 2360 | 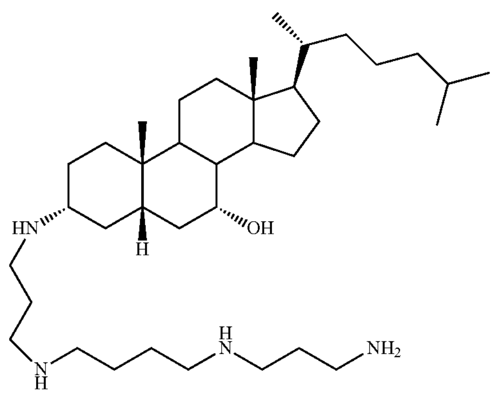 [SMILES: CC(C)CCC[C@@H](C)[C@H]1CCC2C3C(CC[C@@]21C)[C@@]1(C)CC[C@@H](NCCCNCCCCNCCCN)C[C@H]1C[C@H]3O] | 81 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2361 | (structure) | 82 | | | | |
| 2363 | (structure) | 63 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2364 | 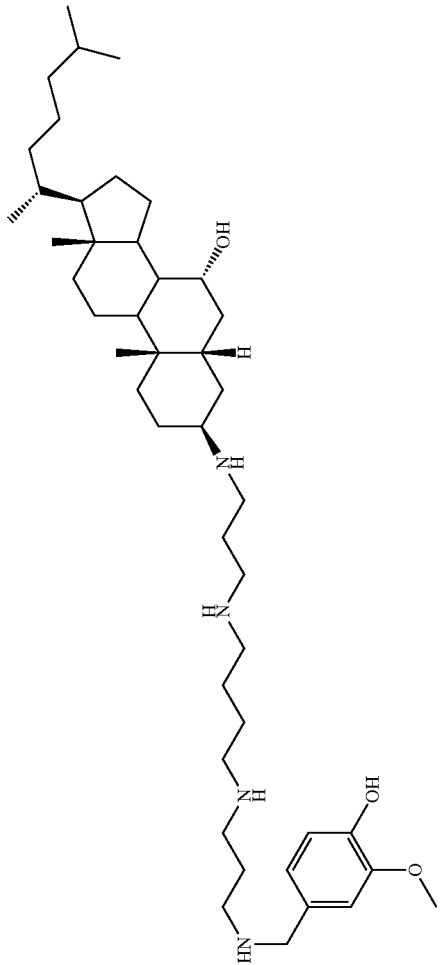 | 61 | | | | |
| 2365 | 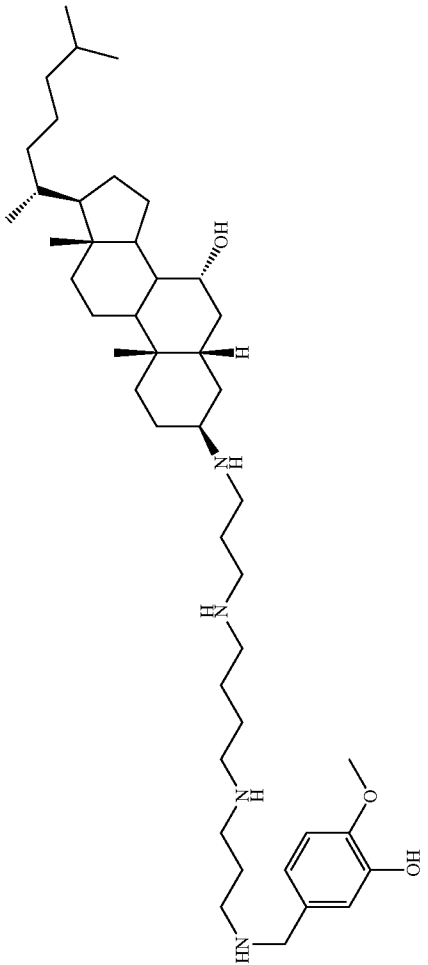 | 73 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2367 | 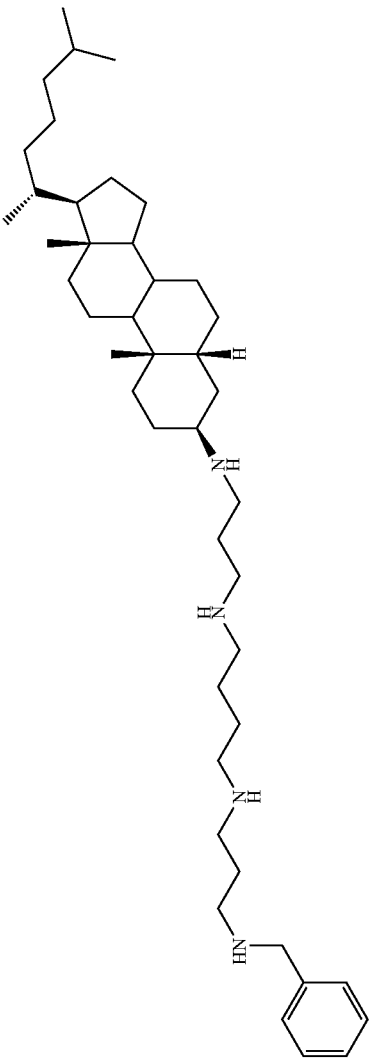 | 78 | | | | |
| 2368 | 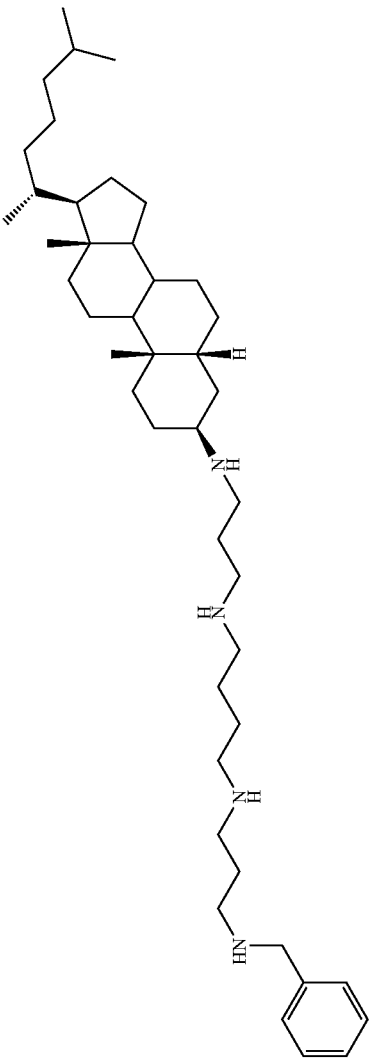 | 37 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2369 | 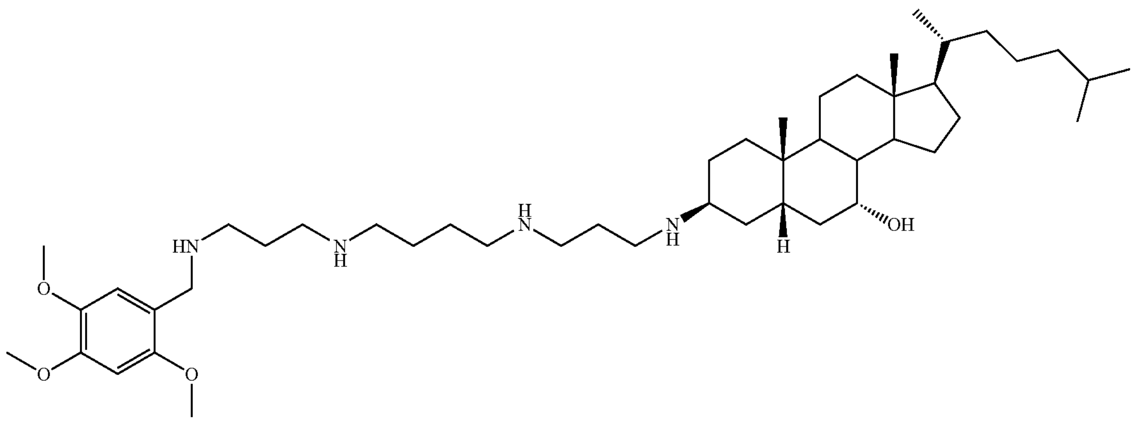 [SMILES: COc1cc(OC)c(OC)cc1CNCCCNCCCCNCCCN[C@H]1CC[C@]2(C)C3CC[C@@]4(C)C(CC[C@@H]4[C@H](C)CCCC(C)C)C3[C@H](O)C[C@@H]2C1] | 93 | | | | |
| 2370 | 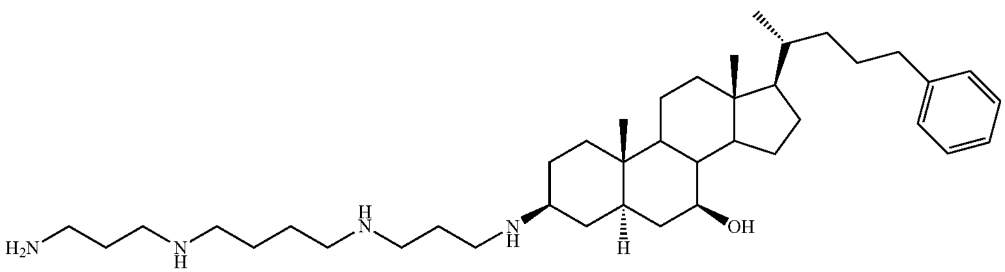 [SMILES: C[C@H](CCCc1ccccc1)[C@H]1CCC2C3C(CC[C@@]21C)[C@@]1(C)CC[C@H](NCCCNCCCCNCCCN)C[C@@H]1C[C@@H]3O] | 77 | | | | |
| 2371 | 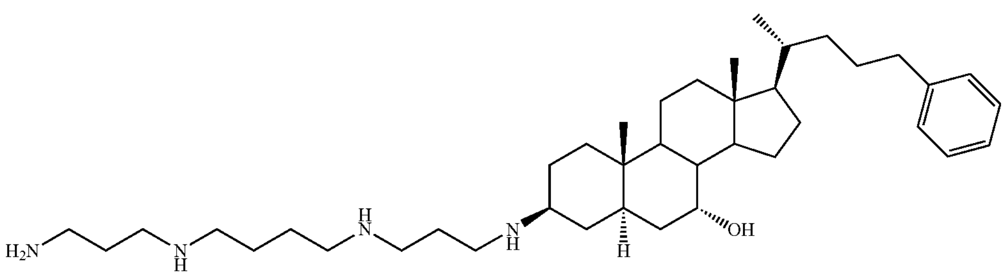 [SMILES: C[C@H](CCCc1ccccc1)[C@H]1CCC2C3C(CC[C@@]21C)[C@@]1(C)CC[C@H](NCCCNCCCCNCCCN)C[C@@H]1C[C@H]3O] | 55 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2374 | 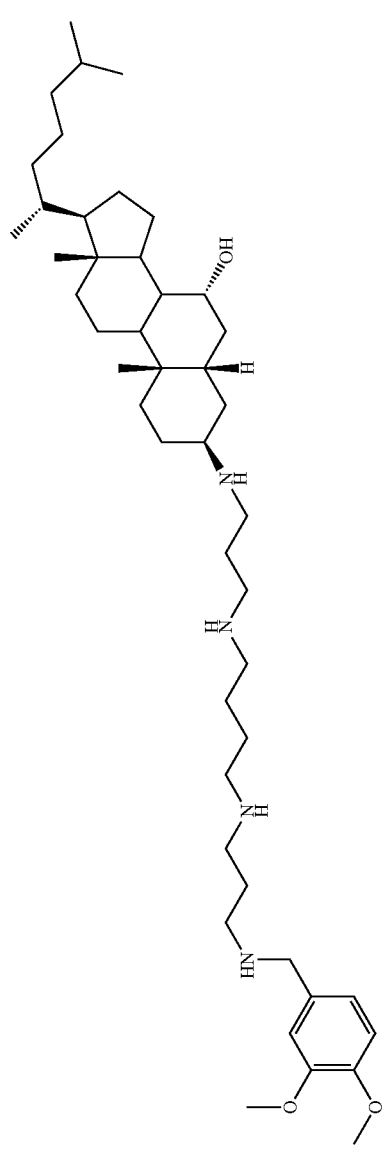 | 37 | | | | |
| 2375 | 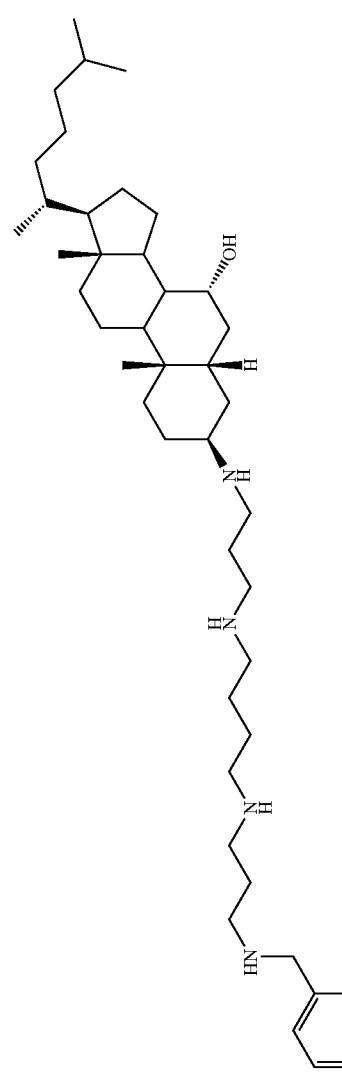 | 59 | | | | |

TABLE 1-continued
| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2450 | 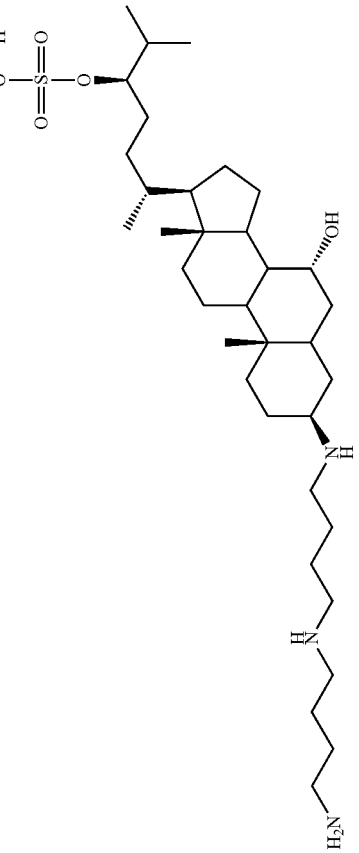 | 28 | | | | |
| 2451 | 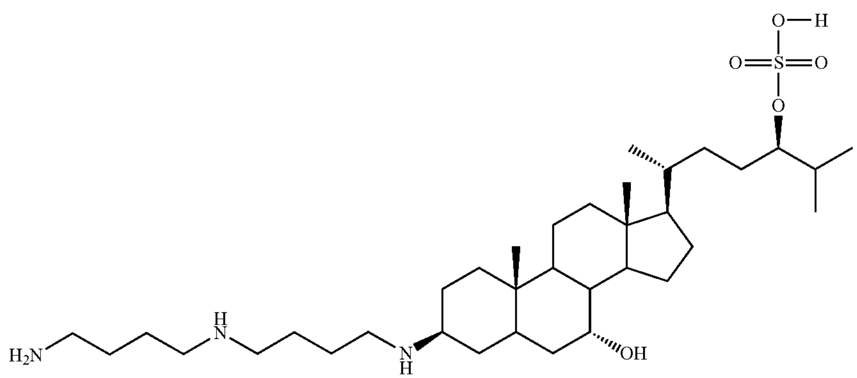 [SMILES: CC(C)[C@@H](CC[C@@H](C)[C@H]1CCC2C3C(CC[C@@]21C)[C@@]1(C)CC[C@H](NCCCCNCCCCN)CC1C[C@H]3O)OS(=O)(=O)O] | 7 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2459 | 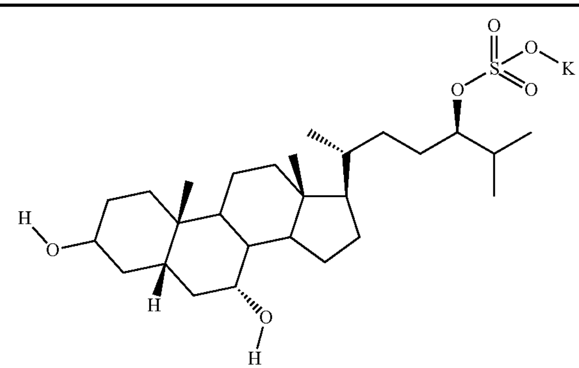 | 17 | | | | |
| 2464 | 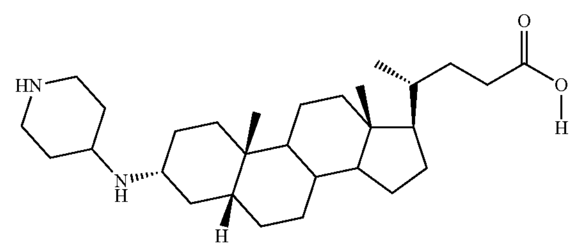 [SMILES: C[C@H](CCC(=O)O)[C@H]1CCC2C3CC[C@@H]4C[C@H](NC5CCNCC5)CC[C@]4(C)C3CC[C@@]21C] | 38 | | | | |
| 2465 | 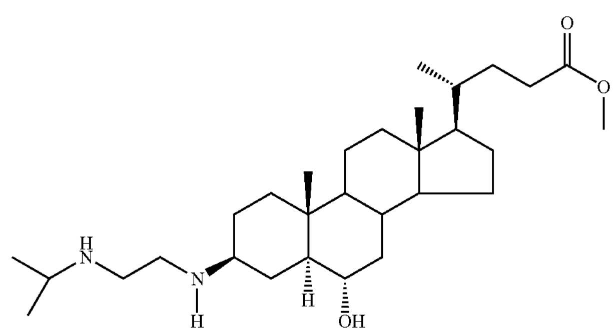 [SMILES: COC(=O)CC[C@@H](C)[C@H]1CCC2C3C[C@H](O)[C@H]4C[C@@H](NCCNC(C)C)CC[C@]4(C)C3CC[C@@]21C] | 10 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2484 | 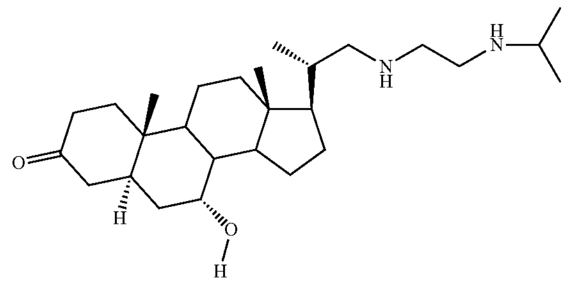 [SMILES: CC(C)NCCNC[C@@H](C)[C@H]1CCC2C3C(CC[C@@]21C)[C@@]1(C)CCC(=O)C[C@@H]1C[C@H]3O] | 5 | | | | |
| 2490 | 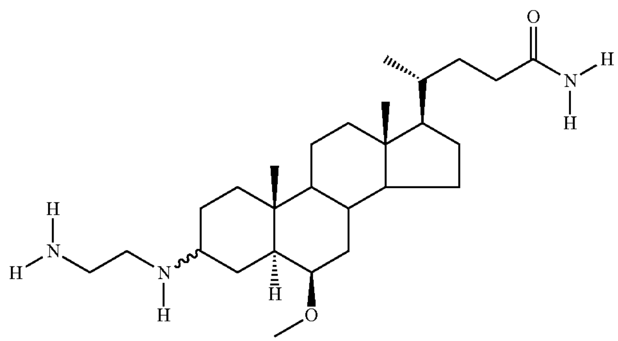 [SMILES: CO[C@@H]1CC2C3CC[C@H]([C@H](C)CCC(N)=O)[C@@]3(C)CCC2[C@@]2(C)CCC(NCCN)C[C@H]12] | 7 | | | | |
| 2491 | 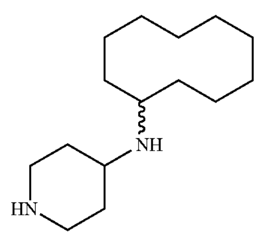 [SMILES: C1CCCCC(NC2CCNCC2)CCCC1] | 9 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2492 | | 10 | | | | |
| 2492 | | 10 | | | | |
| 2493 | 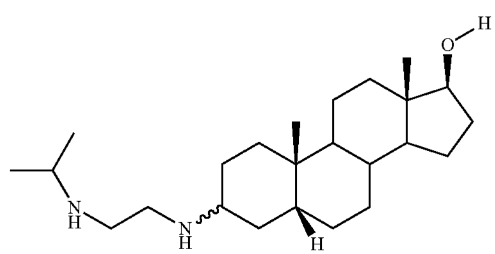 [SMILES: CC(C)NCCNC1CC[C@]2(C)C3CC[C@@]4(C)C(CC[C@@H]4O)C3CC[C@@H]2C1] | 10 | | | | |

TABLE 1-continued

| Compound | Structure | PTP1B Inhibition (5 µM) | TCPTP Inhibition (200 µM) | % Reduction in FBG | % Reduction in OGTT Above Baseline AUC | % Change in Body Weight |
|---|---|---|---|---|---|---|
| 2494 | 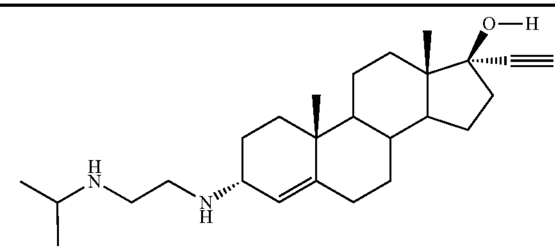 | 9 | | | | |
| 2495 | 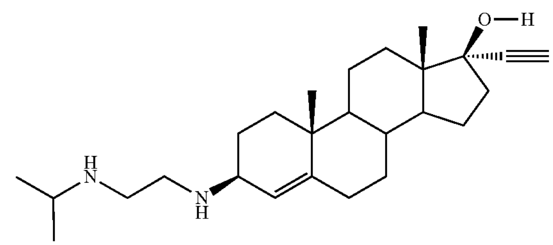 [SMILES: C#C[C@]1(O)CCC2C3CCC4=C[C@@H](NCCNC(C)C)CC[C@]4(C)C3CC[C@@]21C] | 7 | | | | |
| 2496 | 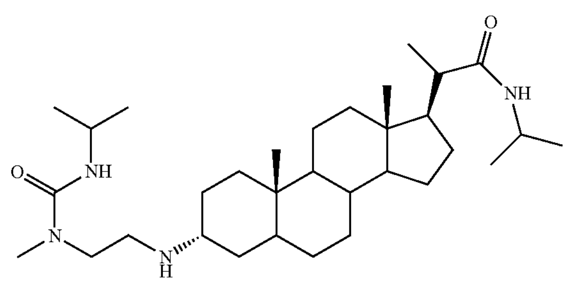 [SMILES: CC(C)NC(=O)C(C)[C@H]1CCC2C3CCC4C[C@H](NCCN(C)C(=O)NC(C)C)CC[C@]4(C)C3CC[C@@]21C] | 10 | | | | |

TABLE 1-continued

| Compound | Structure | PTP1B Inhibition (5 μM) | TCPTP Inhibition (200 μM) | % Reduction in FBG | % Reduction in OGTT Above Baseline AUC | % Change in Body Weight |
|---|---|---|---|---|---|---|
| 2497 | 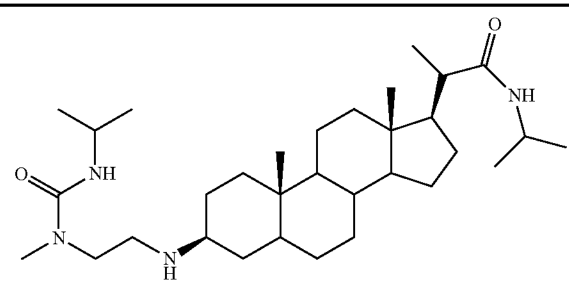 | 15 | | | | |
| 2498 | 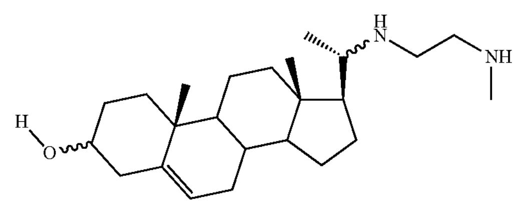 | 13 | | | | |

The invention claimed is:
1. A compound which is
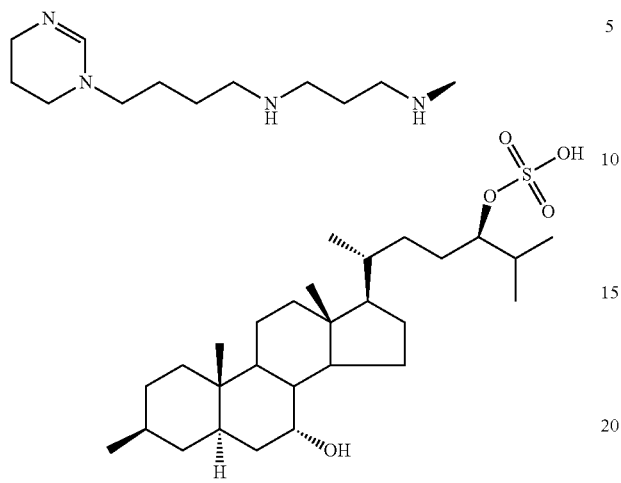
or a pharmaceutically acceptable salt thereof.
2. A compound which is
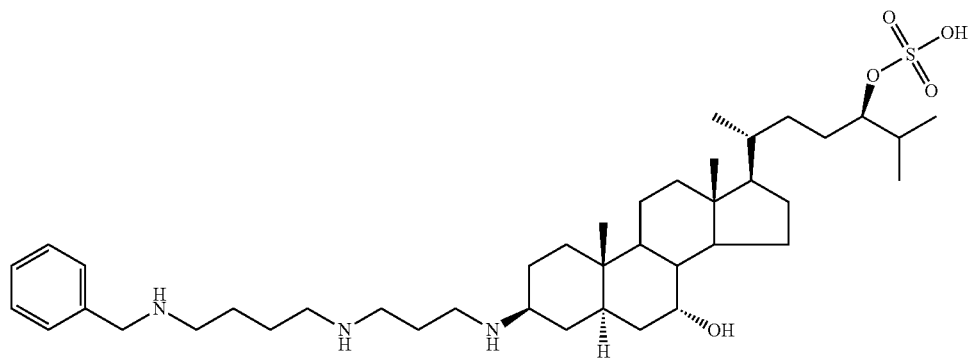 [SMILES: CC(C)[C@@H](CC[C@@H](C)[C@H]1CCC2C3C(CC[C@@]21C)[C@@]1(C)CC[C@H](NCCCNCCCCNCc2ccccc2)C[C@@H]1C[C@H]3O)OS(=O)(=O)O]
or a pharmaceutically acceptable salt thereof.
3. A compound which is
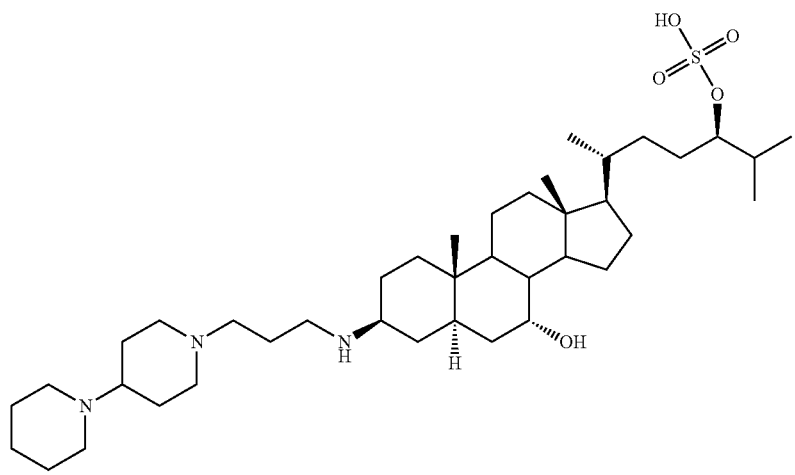 [SMILES: CC(C)[C@@H](CC[C@@H](C)[C@H]1CCC2C3C(CC[C@@]21C)[C@@]1(C)CC[C@H](NCCCN2CCC(N4CCCCC4)CC2)C[C@@H]1C[C@H]3O)OS(=O)(=O)O]
or a pharmaceutically acceptable salt thereof.

4. A compound which is

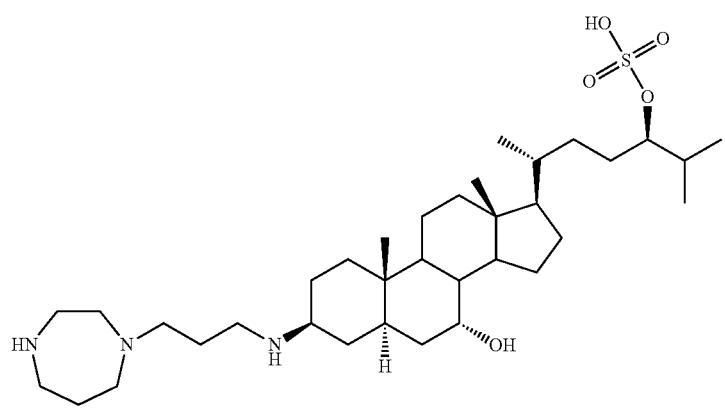 [SMILES: CC(C)[C@@H](CC[C@@H](C)[C@H]1CCC2C3C(CC[C@@]21C)[C@@]1(C)CC[C@H](NCCCN2CCCNCC2)C[C@@H]1C[C@H]3O)OS(=O)(=O)O]

or a pharmaceutically acceptable salt thereof.

5. A pharmaceutical composition comprising the compound of claim 1 and a pharmaceutically acceptable diluent or carrier.

6. A pharmaceutical composition comprising the compound of claim 2 and a pharmaceutically acceptable diluent or carrier.

7. A pharmaceutical composition comprising the compound of claim 3 and a pharmaceutically acceptable diluent or carrier.

8. A pharmaceutical composition comprising the compound of claim 4 and a pharmaceutically acceptable diluent or carrier.

* * * * *